US008926533B2

(12) United States Patent
Bockenstedt et al.

(10) Patent No.: US 8,926,533 B2
(45) Date of Patent: Jan. 6, 2015

(54) THERAPY HEAD FOR USE WITH AN ULTRASOUND SYSTEM

(75) Inventors: Craig Robert Bockenstedt, Kenmore, WA (US); Blake Little, Bothell, WA (US); Ethan Albright, Bothell, WA (US)

(73) Assignee: Liposonix, Inc., Bothell, WA (US)

( * ) Notice: Subject to any disclaimer, the term of this patent is extended or adjusted under 35 U.S.C. 154(b) by 749 days.

(21) Appl. No.: 12/364,327

(22) Filed: Feb. 2, 2009

(65) Prior Publication Data

US 2009/0171252 A1   Jul. 2, 2009

Related U.S. Application Data

(63) Continuation-in-part of application No. 11/027,912, filed on Dec. 29, 2004, now Pat. No. 7,695,437.

(60) Provisional application No. 60/534,036, filed on Dec. 30, 2003, provisional application No. 61/025,618, filed on Feb. 1, 2008.

(51) Int. Cl.
*A61H 1/00* (2006.01)
*A61N 7/02* (2006.01)
*A61B 19/00* (2006.01)
*A61H 23/02* (2006.01)
*A61N 7/00* (2006.01)

(52) U.S. Cl.
CPC . *A61N 7/02* (2013.01); *A61B 19/22* (2013.01); *A61H 23/0245* (2013.01); *A61N 2007/0008* (2013.01); *A61B 2007/0091* (2013.01)
USPC .............................................................. 601/2

(58) Field of Classification Search
CPC .............................. A61N 7/00; A61H 23/0245
USPC .............................................................. 601/2
See application file for complete search history.

(56) References Cited

U.S. PATENT DOCUMENTS 3,454,923 A   7/1969   Currie
4,002,221 A   1/1977   Buchalter
(Continued)

FOREIGN PATENT DOCUMENTS

DE   3227624 A1   1/1984
DE   19745400 C1   4/1999
(Continued)

OTHER PUBLICATIONS

Adams et al., "Chronic Response of Normal Porcine Fat and Muscle to Focused Ultrasound Hyperthermia," *Radiation Research*, (1985), vol. 104, pp. 140-152.

(Continued)

*Primary Examiner* — Tse Chen
*Assistant Examiner* — Hien Nguyen
(74) *Attorney, Agent, or Firm* — Wood, Herron & Evans, LLP

(57) ABSTRACT

Therapy heads and related medical systems having an actuation assembly for controlling the position/orientation of a directional energy applicator in at least two planes are disclosed. A therapy head includes an enclosure, a partition separating a lower compartment from an upper compartment, an aperture in the partition, a control arm extending through the aperture, an actuation assembly positioned within the upper compartment, and a directional energy applicator positioned in the lower compartment for transmitting energy through a window. The control arm includes an upper end disposed within the upper compartment and a lower end disposed within the lower compartment. The actuation assembly is coupled with the upper end of the control arm such that the control arm is movable by the actuation assembly in at least two planes. The directional energy applicator is coupled with the lower end of the control arm.

20 Claims, 17 Drawing Sheets

(56) References Cited

U.S. PATENT DOCUMENTS

| | | | |
|---|---|---|---|
| 4,059,098 A | 11/1977 | Murdock | |
| 4,211,949 A | 7/1980 | Brisken et al. | |
| 4,291,578 A | 9/1981 | Hetz et al. | |
| 4,326,418 A | 4/1982 | Pell, Jr. | |
| 4,368,410 A | 1/1983 | Hance et al. | |
| 4,437,033 A | 3/1984 | Diepers | |
| 4,459,854 A | 7/1984 | Richardson et al. | |
| 4,501,557 A | 2/1985 | Tamura et al. | |
| 4,541,434 A * | 9/1985 | Okado | 600/446 |
| 4,556,066 A | 12/1985 | Semrow | |
| 4,567,895 A | 2/1986 | Putzke | |
| 4,572,200 A * | 2/1986 | Schroeder et al. | 600/446 |
| 4,593,699 A | 6/1986 | Poncy et al. | |
| 4,756,313 A * | 7/1988 | Terwilliger | 600/462 |
| 4,865,042 A | 9/1989 | Umemura et al. | |
| 4,895,158 A * | 1/1990 | Kawabuchi et al. | 600/463 |
| 4,930,515 A | 6/1990 | Terwilliger | |
| 4,936,303 A | 6/1990 | Detwiler et al. | |
| 4,955,365 A * | 9/1990 | Fry et al. | 601/2 |
| 4,960,107 A | 10/1990 | Aida et al. | |
| 5,259,383 A | 11/1993 | Holstein et al. | |
| 5,301,660 A | 4/1994 | Rattner | |
| 5,331,962 A | 7/1994 | Coleman et al. | |
| 5,352,301 A | 10/1994 | Panchanathan et al. | |
| 5,382,286 A | 1/1995 | Fanning et al. | |
| 5,419,327 A | 5/1995 | Rohwedder et al. | |
| 5,434,208 A | 7/1995 | Batelaan et al. | |
| 5,476,438 A | 12/1995 | Edrich et al. | |
| 5,477,736 A | 12/1995 | Lorraine | |
| 5,505,206 A | 4/1996 | Walloch | |
| 5,526,815 A | 6/1996 | Granz et al. | |
| 5,568,810 A | 10/1996 | Hamers et al. | |
| 5,623,928 A | 4/1997 | Wright et al. | |
| 5,626,554 A | 5/1997 | Ryaby et al. | |
| 5,669,150 A | 9/1997 | Guertin et al. | |
| 5,676,159 A | 10/1997 | Navis | |
| 5,722,411 A | 3/1998 | Suzuki et al. | |
| 5,738,098 A | 4/1998 | Brock-Fisher et al. | |
| 5,738,635 A | 4/1998 | Chapelon et al. | |
| 5,755,753 A | 5/1998 | Knowlton | |
| 5,759,162 A | 6/1998 | Oppelt et al. | |
| 5,769,790 A | 6/1998 | Watkins et al. | |
| 5,820,623 A | 10/1998 | Ng | |
| 5,871,446 A | 2/1999 | Wilk | |
| 5,938,608 A | 8/1999 | Bieger et al. | |
| 5,938,922 A | 8/1999 | Fulk, Jr. et al. | |
| 6,039,689 A | 3/2000 | Lizzi | |
| 6,039,694 A | 3/2000 | Larson et al. | |
| 6,085,749 A | 7/2000 | Wardle et al. | |
| 6,113,558 A | 9/2000 | Rosenschein et al. | |
| 6,142,748 A | 11/2000 | Harris et al. | |
| 6,152,137 A | 11/2000 | Schwartz et al. | |
| 6,217,515 B1 | 4/2001 | Yamakawa et al. | |
| 6,233,476 B1 | 5/2001 | Strommer et al. | |
| 6,261,249 B1 | 7/2001 | Talish et al. | |
| 6,264,605 B1 | 7/2001 | Scirica et al. | |
| 6,302,848 B1 | 10/2001 | Larson et al. | |
| 6,306,146 B1 | 10/2001 | Dinkler | |
| 6,325,769 B1 | 12/2001 | Klopotek | |
| 6,350,245 B1 | 2/2002 | Cimino | |
| 6,366,831 B1 | 4/2002 | Raab | |
| 6,419,648 B1 | 7/2002 | Vitek et al. | |
| 6,423,077 B2 | 7/2002 | Carol et al. | |
| 6,488,639 B1 | 12/2002 | Ribault et al. | |
| 6,503,205 B2 | 1/2003 | Manor et al. | |
| 6,506,171 B1 | 1/2003 | Vitek et al. | |
| 6,554,826 B1 | 4/2003 | Deardorff | |
| 6,561,389 B1 | 5/2003 | Earle | |
| 6,575,906 B1 | 6/2003 | Schembri, Jr. et al. | |
| 6,607,498 B2 | 8/2003 | Eshel | |
| 6,613,004 B1 | 9/2003 | Vitek et al. | |
| 6,618,620 B1 | 9/2003 | Freundlich et al. | |
| 6,778,848 B1 | 8/2004 | Bechtold et al. | |
| 7,255,678 B2 | 8/2007 | Mehi et al. | |
| 7,494,466 B2 | 2/2009 | Chauhan et al. | |
| 7,695,437 B2 | 4/2010 | Quistgaard et al. | |
| 8,282,554 B2 | 10/2012 | Makin et al. | |
| 2002/0042574 A1 | 4/2002 | Manor et al. | |
| 2002/0055736 A1 * | 5/2002 | Horn et al. | 606/26 |
| 2002/0128592 A1 | 9/2002 | Eshel | |
| 2003/0004439 A1 | 1/2003 | Pant et al. | |
| 2003/0018255 A1 | 1/2003 | Martin et al. | |
| 2003/0083536 A1 | 5/2003 | Eshel et al. | |
| 2004/0122319 A1 | 6/2004 | Mehi et al. | |
| 2004/0204650 A1 | 10/2004 | Taylor | |
| 2005/0154431 A1 | 7/2005 | Quistgaard et al. | |
| 2006/0122509 A1 | 6/2006 | Desilets | |
| 2009/0171252 A1 | 7/2009 | Bockenstedt et al. | |

FOREIGN PATENT DOCUMENTS

| | | |
|---|---|---|
| EP | 0 253 268 A1 | 7/1987 |
| GB | 820814 | 9/1959 |
| JP | 7047078 A | 2/1995 |
| JP | 9047458 A | 2/1997 |
| JP | 2000175933 A | 6/2000 |
| JP | 2000237199 A | 9/2000 |
| JP | 2001327495 A | 11/2001 |
| WO | WO 02/24076 A1 | 3/2002 |
| WO | 02054018 A2 | 7/2002 |
| WO | 03/059434 A2 | 7/2003 |

OTHER PUBLICATIONS

Ayme et al., "Occurrence of Transient Cavitation in Pulsed Sawtooth Ultrasonic Fields," *J. Acoust. Soc. Am.*, (Nov. 1988), vol. 84, No. 5, pp. 1598-1605.

Billard et al., "Effects of Physical Parameters on High Temperature Ultrasound Hyperthermia," *Ultrasound Med Biol.*, (1990), vol. 16, No. 4, pp. 409-420.

Chen et al., "Mechanisms of Lesion Formation in High Intensity Focused Ultrasound Therapy," *Proc. IEEE Ultrason. Symp.*, (Oct. 2002), vol. 2, pp. 1443-1446.

Chongqing Haifu (HIFU) Technology Co., Ltd., [Brochure], "Haifu: Brief Introduction of the Company," pp. 1-26.

Clarke et al., "Physical and Chemical Aspects of Ultrasonic Disruption of Cells," *J. Acoust. Soc. Am.*, (Feb. 1970), vol. 47, No. 2B, pp. 649-653.

Fjield et al., "In Vivo Verification of the Acoustic Model Used to Predict Temperature Elevations for MRI Guided Ultrasound Surgery," *Proc. IEEE Ultrason. Symp.*, (1998), vol. 2, pp. 1415-1418.

Flynn et al, "A Mechanism for the Generation of Cavitation Maxima by Pulsed Ultrasound," *J. Acoust. Soc. Am.*, (Aug. 1984), vol. 76, No. 2, pp. 505-512.

Fry et al., "Threshold Ultrasonic Dosages for Structural Changes in the Mammalian Brain," *Acoust. Soc. Am.*, (Dec. 1970), vol. 48, No. 6B, pp. 1413-1417.

Haar, "Ultra sound Focal Beam Surgery," *Ultrasound Med Biol.*, (1995), vol. 21, No. 9, pp. 1089-1100.

Hand, "Ultrasound Hyperthermia and the Prediction of Heating," Chapter 8, *Ultrasound in Medicine*, eds. Duck et al., Inst of Physics Pub Inc, Bristol, (Dec. 1998), pp. 151-157.

Hoffelner et al., "Self-Focusing HIFU Source for Large Therapy Volumes," Ultrasonics Symposium, *Proc. IEEE Ultrason. Symp* (1998), vol. 2, pp. 1563-1566.

Kinney, "Body Contouring with External Ultrasound," *Plastic & Reconstructive Surgery*, (Feb. 1999),vol. 103, No. 2, pp. 728-729.

Lele, "Thresholds and mechanisms of ultrasonic damage to "organized" animal tissues," Proc Symp Biol Eff Character Ultrasound Sources, (Jun. 2-3, 1977), Rockville, Maryland, (Dec. 1977), pp. 224-239.

Padmaker, Thresholds and mechanisms of ultrasonic damage to 'organized' animal tissues *Symposium on Biological Effects and Characterizations of Ultrasound Sources* (1977) Hazzard et al., Eds., pp. 224-239.

Supplementary Search Report of European Patent Application No. 04816028.7, mailed Nov. 3, 2010, 3 pages total.

Canadian Intellectual Property Office, Official Action issued in related Canadian application No. 2,551,348 dated Apr. 17, 2012.

Official Action issued in related U.S. Appl. No. 12/961,102 mailed on Dec. 5, 2012 (12 pages).

(56) References Cited

OTHER PUBLICATIONS

USPTO, Office Action issued in U.S. Appl. No. 12/961,102 dated Apr. 12, 2013.
Final Rejection issued in related Japanese Patent Application No. 2006-547594 dated Dec. 2, 2011.
Official Action issued in related Japanese Patent Application No. 2006-547594 dated Mar. 23, 2011.
Official Action issued in related Japanese Patent Applicaton No. 2006-547594 dated Jun. 1, 2010.
USPTO, Office Action issued in U.S. Appl. No. 12/961,102 dated Sep. 19, 2014.

* cited by examiner

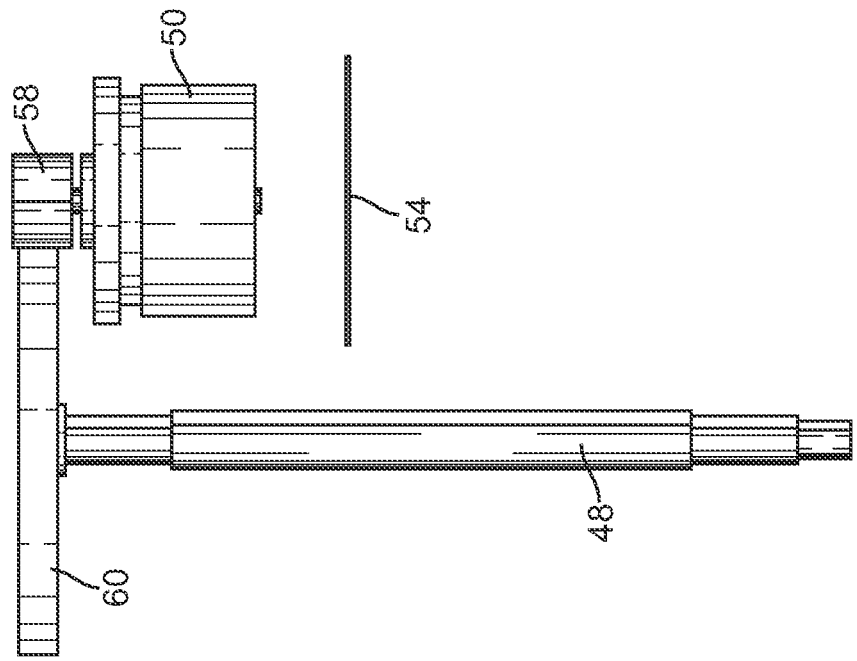
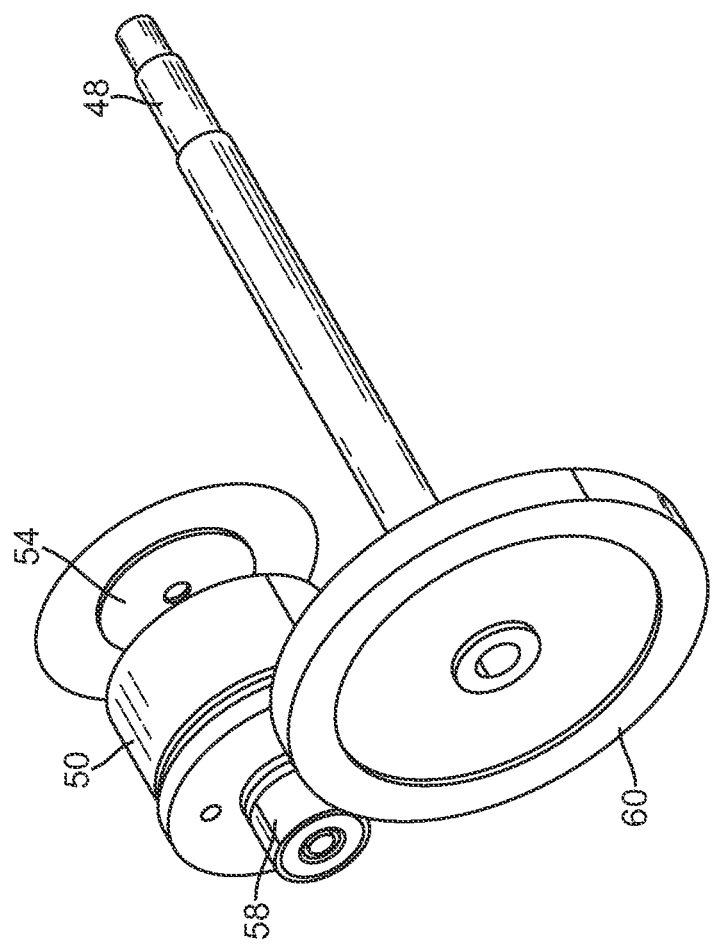

THERAPY HEAD FOR USE WITH AN ULTRASOUND SYSTEM

CROSS-REFERENCES TO RELATED APPLICATIONS

The present application is a continuation-in-part of application Ser. No. 11/027,912, filed on Dec. 29, 2004, which claims the benefit of provisional application No. 60/534,036, filed on Dec. 30, 2003, the full disclosures of which are incorporated herein by reference. The present application also claims the benefit of provisional application No. 61/025,618, filed on Feb. 1, 2008, the full disclosure of which is incorporated herein by reference.

BACKGROUND

The present invention relates generally to handheld medical devices for precisely delivering energy into a human body, and more particularly to handheld medical devices and related systems having an actuation assembly for controlling the position/orientation of a directional energy applicator in at least two planes. The position/orientation control provided can be especially beneficial when used in a medical ultrasound therapy head that is used for non-invasive therapies.

A general problem in the application of high intensity focused ultrasound (HIFU) for therapeutic purposes is that it is often necessary to hold the therapeutic means stationary for some significant amount of time over the tissue to be treated. Alternatively, it may be necessary to scan the therapy beam at a slow, constant rate through the tissue to be treated. Both of these requirements present a barrier to the use of hand-held therapeutic devices, as it is often difficult or impossible for a person to either hold the device steady, or to scan at an acceptably slow and steady rate for the desired therapeutic effect.

A HIFU procedure may require that the ultrasound beam be scanned over the treatment volume at a constant rate (e.g., 5 mm/sec+/−1 mm/sec) to achieve the desired therapeutic effect. Additionally, the treatment volume must be scanned so that there is never more than a 2 mm spacing between adjacent focal lines of treatment. These requirements are beyond the capabilities of most human beings. The solution in the past has been to incorporate a computer controlled motion device rigidly mounted to something that is stationary with respect to the patient (e.g., the floor, wall or bed). Such a device is either absolutely stationary, or is able to scan at a precise rate in a precise pattern without any human intervention. Such an arrangement has the disadvantages of size and bulk, complexity and reliability of the overall device.

Thus there remains a need in the art for a HIFU applicator that can be easily manipulated by a user while still providing reliable and uniform treatment.

There is also a need for a HIFU transducer that can keep track of the tissue volumes treated so as to prevent re-treatment of those same volumes.

There is still further a need for a therapy device that can assist the operator in identifying regions of tissue to be treated.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Hand held therapy heads and related medical systems are provided that include an actuation assembly for selectively directing the output of an directional energy applicator, such as an ultrasound transducer. Such selective direction can be used during ultrasound therapies to increase the accuracy by which the energy is delivered over a treatment region, which may result in improved therapeutic effect.

In an embodiment, a therapy head is provided. The therapy head includes an enclosure adapted to be manipulated by hand, a partition separating a lower compartment of the enclosure from an upper compartment of the enclosure, an aperture in the partition, a control arm extending through the aperture, an actuation assembly positioned within the upper compartment, and a directional energy applicator for transmitting energy through a window included within the lower compartment. The control arm includes an upper end disposed within the upper compartment and a lower end disposed within the lower compartment. The control arm is movable within the aperture while the aperture is sealed between the upper and lower compartments. The actuation assembly is coupled with the upper end of the control arm such that the control arm is movable by the actuation assembly in at least two planes. The directional energy applicator is coupled with the lower end of the control arm.

In another embodiment, a therapy head is provided. The therapy head includes an enclosure adapted to be manipulated by hand, a directional energy applicator disposed within the enclosure, and a means for maneuvering the directional energy applicator within the enclosure so as to direct the energy applicator over a two-dimensional treatment area. The enclosure includes a window through which the directional energy applicator transmits energy.

In another embodiment, a medical ultrasound system is provided. The medical ultrasound system includes a base unit movable to along side a patient, and an ultrasound head coupled with the base unit. The ultrasound head includes an enclosure adapted to be manipulated by hand, a partition separating a lower compartment of the enclosure from an upper compartment of the enclosure, an aperture in the partition, a control arm extending through the aperture, an actuation assembly positioned within the upper compartment, and an ultrasound transducer for transmitting ultrasound energy through a window included within the lower compartment. The control arm includes an upper end disposed within the upper compartment and a lower end disposed within the lower compartment. The control arm is movable within the aperture while the aperture is sealed between the upper and lower compartments. The actuation assembly is coupled with the upper end of the control arm such that the control arm is movable by the actuation assembly in at least two planes. The ultrasound transducer is coupled with the lower end of the control arm.

For a fuller understanding of the nature and advantages of the present invention, reference should be made to the ensuing detailed description and accompanying drawings. Other aspects, objects and advantages of the invention will be apparent from the drawings and the detailed description that follows.

BRIEF DESCRIPTION OF THE DRAWINGS

FIG. 6A is a perspective view of a central shaft and associated drive motor of the actuation assembly of FIG. 5.

FIG. 6B is a top view of the central shaft and associated drive motor of the actuation assembly of FIG. 5.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Described herein are various embodiments of a therapy head for use with a medical system. More particularly, therapy heads and related medical systems are provided that include an actuation assembly for selectively directing the output of an directional energy applicator, such as an ultrasound transducer.

Figure 1:
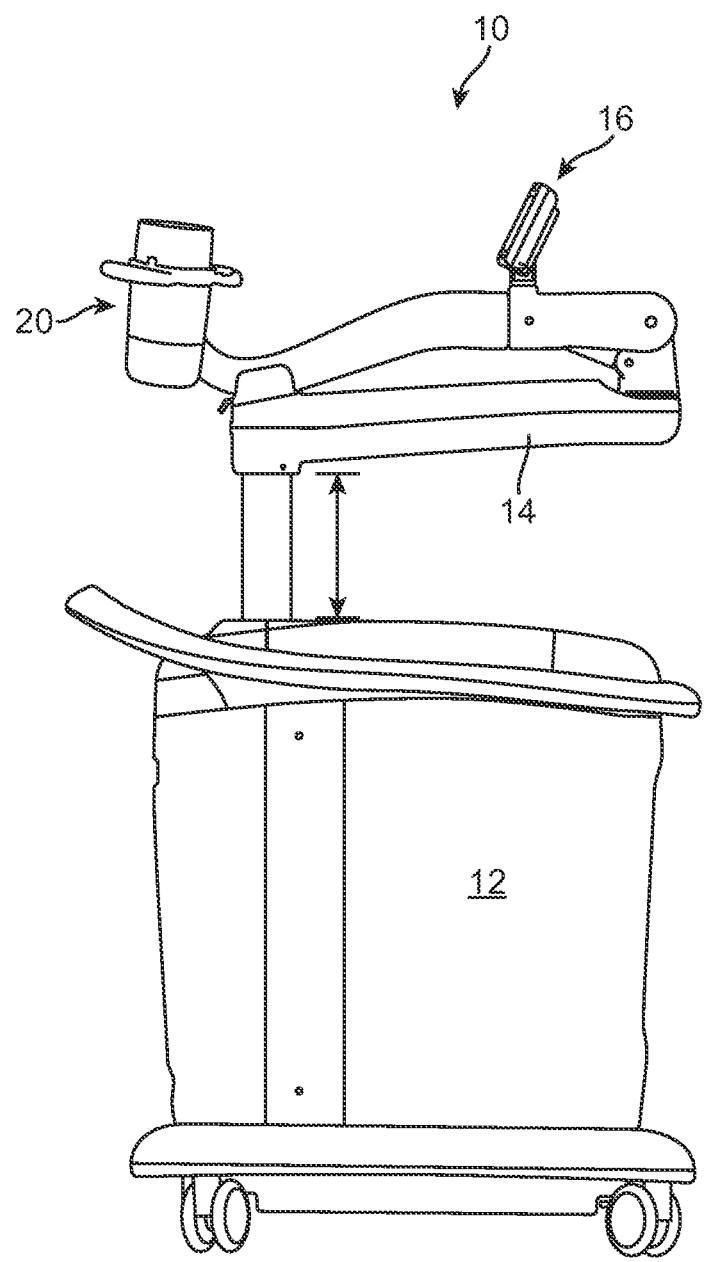
FIG. 1 shows a medical ultrasound therapy system in accordance with an embodiment.

Referring now to the drawings, in which like reference numerals represent like parts throughout the several views, FIG. 1 shows a medical ultrasound system 10. The medical ultrasound system 10 includes a base unit 12, an articulating arm 14 attached to the base unit, and a user interface device 16 attached to the articulating arm 14. At the distal end of the articulating arm 14 is an ultrasound head 20.

Figure 2:
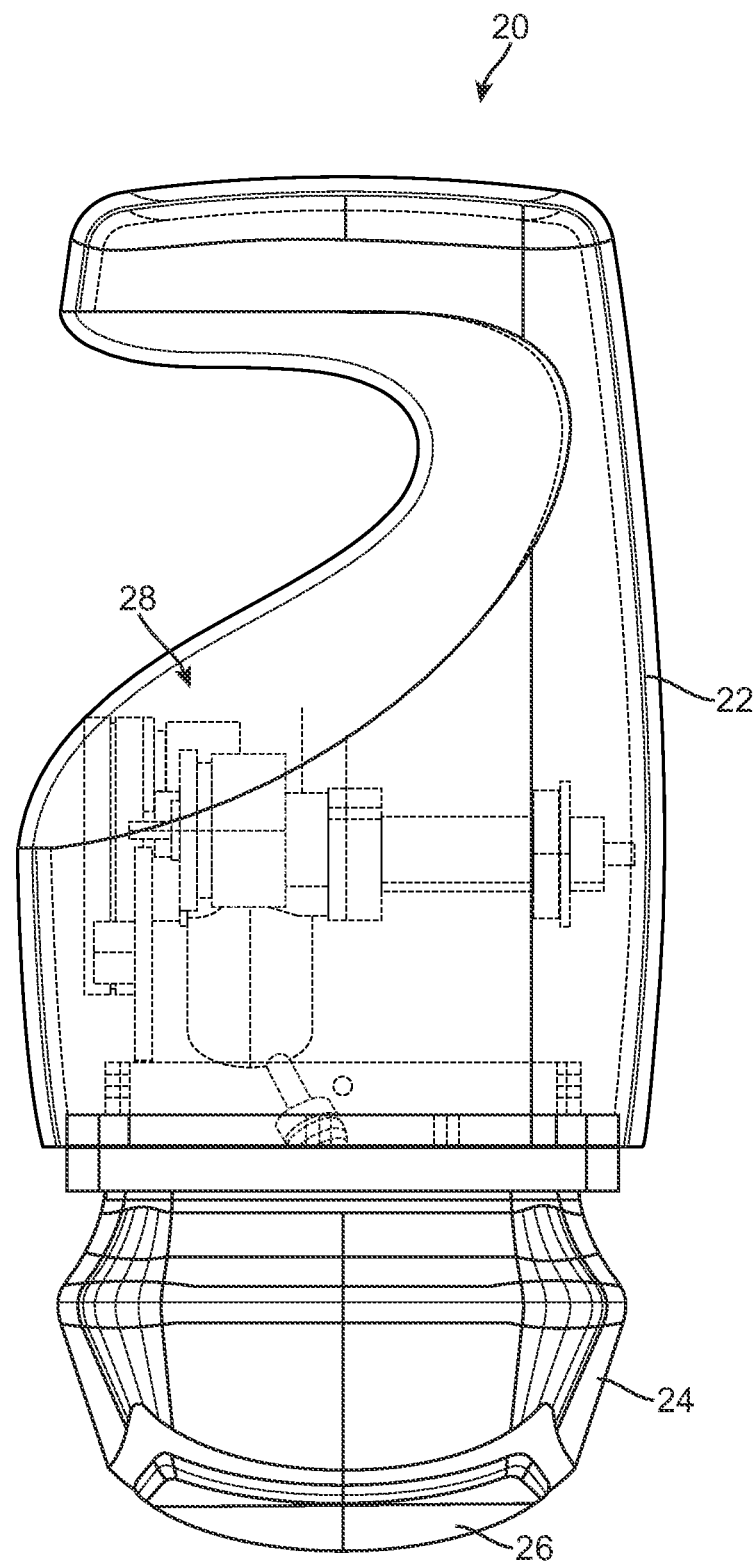
FIG. 2 shows an ultrasound therapy head having an actuation assembly for varying the position/orientation of an ultrasound transducer in accordance with an embodiment.

The exterior of the ultrasound head 20 is desirably a form factor that is easily handled by an operator. An example of one embodiment is shown in FIG. 2, but the ultrasound head may take many other forms. The ultrasound head 20 may have cables extending from it and going to the base unit 12 through the articulating arm 14, or the cables may optionally be exposed.

As shown in FIG. 2, the ultrasound head 20 includes an upper compartment 22, and a lower compartment 24, or cap. The upper compartment 22 is desirably dry and houses wires, cables, a motor assembly, and/or other features for a transducer, which is mounted in the lower compartment 24. The lower compartment 24 preferably contains a coupling fluid, such as degassed water, used to transfer ultrasound energy from the transducer to and through a window 26 located near the bottom of the lower compartment. Disposed within the upper compartment 22 is an actuation assembly 28. The actuation assembly 28 provides for control over the position/orientation of the transducer located within the lower compartment 24.

In operation, a technician rolls the medical ultrasound system 10 to adjacent a patient. The technician grasps and moves the ultrasound head 20, with the ultrasound head 20 remaining attached to the articulating arm 14. The ultrasound head 20 is aligned so that the window 26 is in contact with the patient. The user interface device 16 may be operated to generate an appropriate treatment or diagnostic test. During use, the transducer mounted in the lower compartment 24 generates ultrasound energy, which may be used, for example, for the destruction of adipose tissue, as described in U.S. Published Application No. 2006/0122509. The actuation assembly 28 can be used to provide for simplified treatment procedures. For example, the ultrasound head 20 can be held in stationary contact with the patient while the actuation assembly 28 varies the position/orientation of the ultrasound transducer so as to apply therapeutic treatment to a local region of the patient using a scan pattern that provides a desired coverage, duration, spacing, etc.

Figure 3:
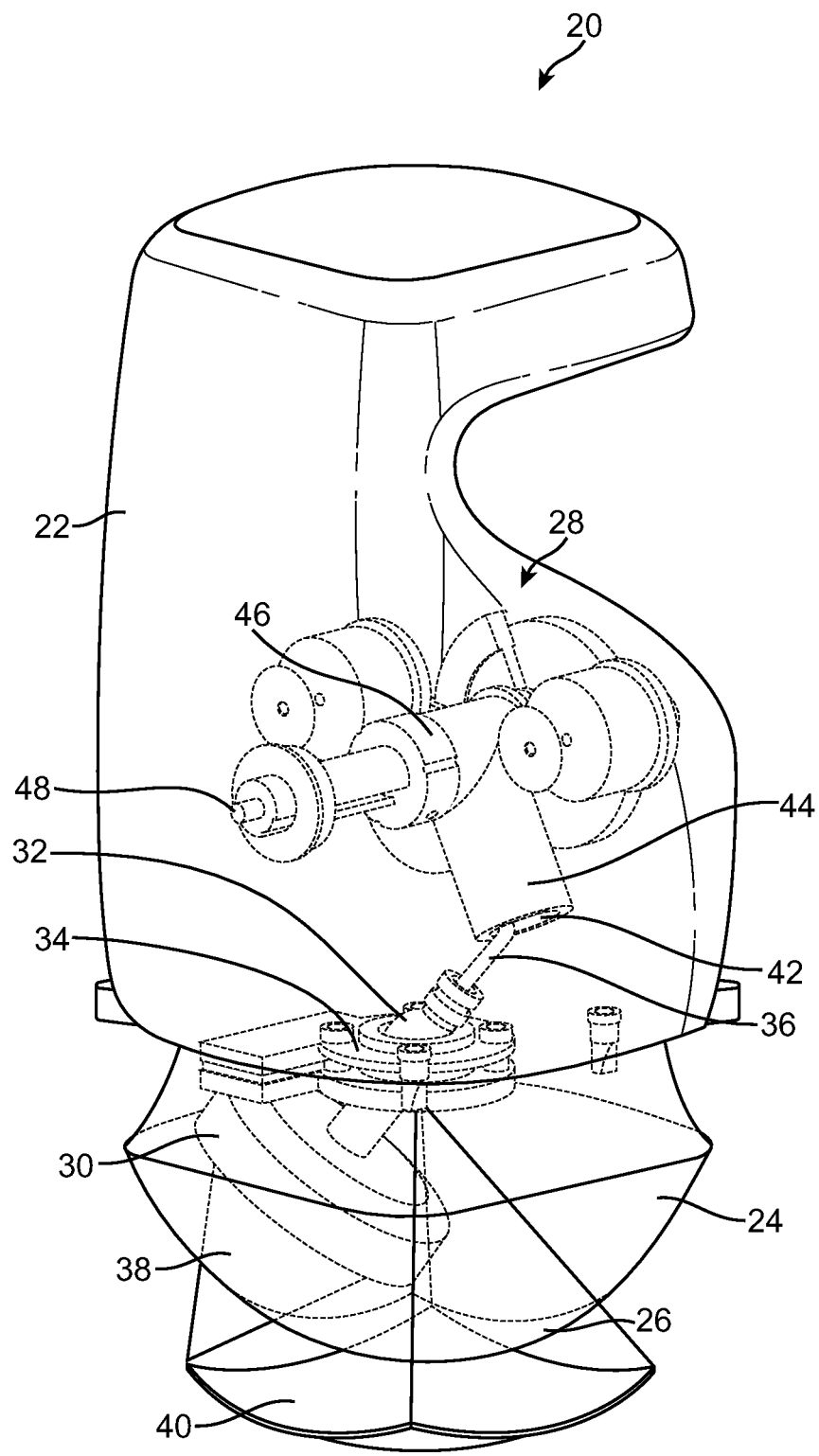
FIG. 3 is a perspective view showing internal assemblies of the ultrasound therapy head of FIG. 2.

FIG. 3 illustrates internal assemblies of the therapy head 20 of FIG. 2. Mounted within the upper compartment 22 is the actuation assembly 28. The actuation assembly 28 is coupled with a ultrasound transducer assembly 30 by way of a control arm 32. The control arm 32 is configured to interface with and pivot within a receptacle 34 that is coupled with a partition that separates the upper compartment 22 from the lower compartment 24. The lower compartment 24 is a sealed assembly that contains a coupling fluid, such as degassed water, that is used to transfer ultrasound energy transmitted by the transducer assembly 30. The receptacle 34 includes at least one fluid seal (e.g., a o-ring seal, a blade seal, etc.) to prevent fluid from entering the upper compartment 22 from the lower compartment 24. The control arm 32 includes a control arm upper end 36 disposed within the upper compartment 22. In the position/orientation shown, the ultrasound transducer assembly 30 is shown as transmitting focused ultrasound energy through the window 26 as illustrated by the ultrasound energy profile 38.

The actuation assembly 28 is operable to move the control arm upper end 36 so as to pivot the control arm 32 within the receptacle 34. The range of motion of the actuation assembly and the control arm 32 produces a coverage area 40 within which focused ultrasound energy can be directed in a controlled fashion (e.g., by using scanning patterns, scanning rates, energy transmission levels, etc.).

Figure 4:
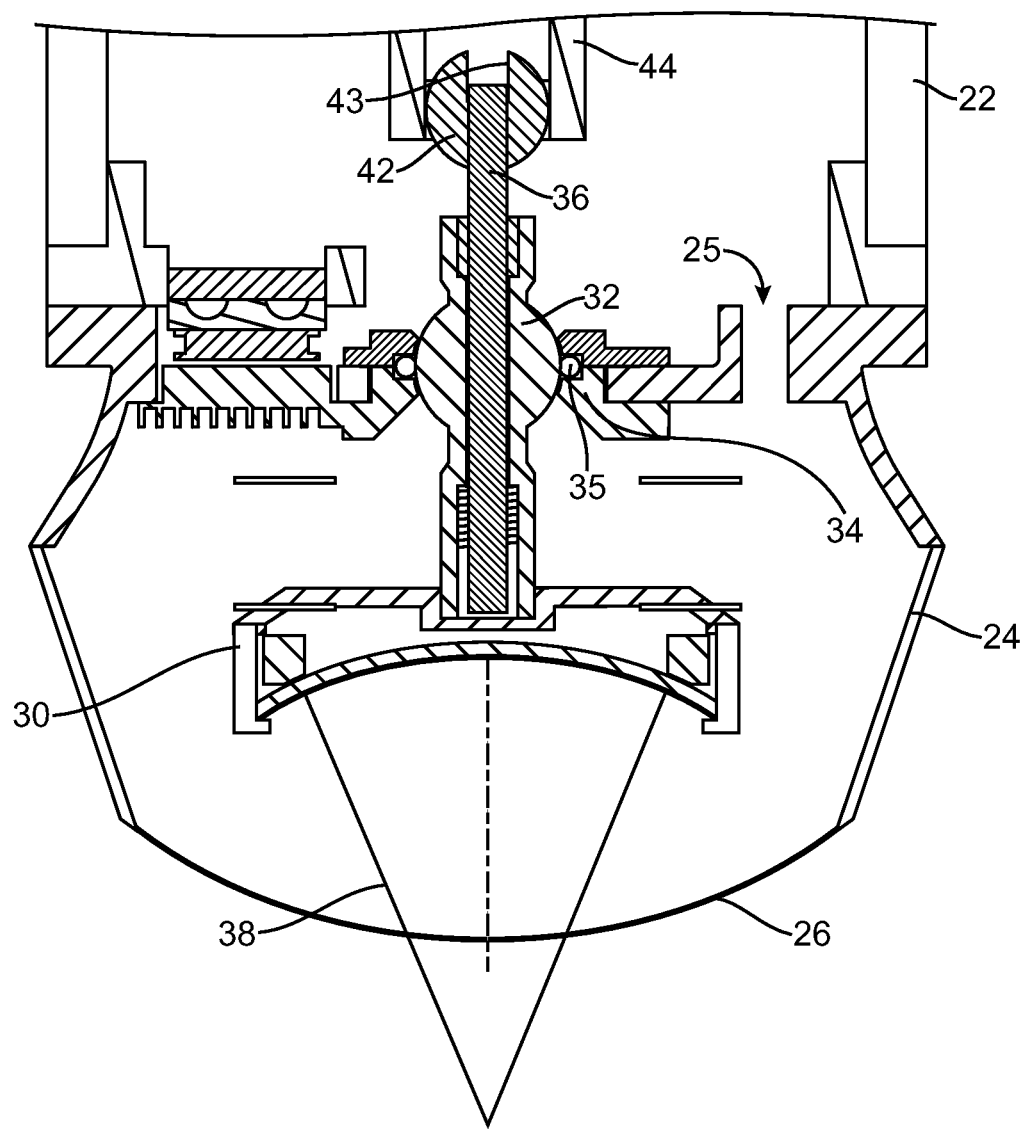
FIG. 4 is a cross-sectional view showing details of an articulated ultrasound transducer assembly coupled with a therapy head partition in accordance with an embodiment.

The control arm upper end 36 is coupled with the actuation assembly 28 by way of a pivot ball 42 (as best shown in FIG. 4), which is received within and positioned by a control arm interface component 44. The control arm interface component 44 is coupled with a translating/rotating hub 46, which directly controls the position/orientation of the control arm interface component 44. The translating/rotating hub 46 is interfaced with a central shaft 48 so that rotation of the central shaft 48 controls the position of the translating/rotating hub 46 along the centerline of the actuation assembly 28. As used herein, the centerline of the actuation assembly 28 is a reference axis that is aligned with the centerline of the actuation assembly 28. A variety of interface configurations can be used to interface the hub 46 with the central shaft 48 so that rotation of the central shaft 48 causes translation of the hub 46 along the centerline of the actuation assembly 28 (e.g., an acme screw assembly, a ball-screw assembly, etc.). As will be describe in detail below, the actuation assembly 28 is configured to rotate the hub 46 through a range of rotation about the centerline of the actuation assembly 28. The combination of translation of the hub 46 along the centerline of the actuation assembly 28 and rotation of the hub 46 about the centerline of the actuation assembly 28 provides a range of motion to the control arm interface component 44 required to direct the ultrasound transducer assembly to any point within the coverage area 40.

FIG. 4 illustrates the details of the articulated ultrasound transducer assembly 30 coupled with a therapy head partition and with the control arm interface component 44. The ultrasound transducer assembly 30 is coupled with the control arm 32 so as to be positioned/oriented within the lower compartment 24. The control arm 32 is constrained by the receptacle 34 such that an instantaneous center of rotation for the control arm 32 is restrained from translating relative to the receptacle 34. The receptacle 34 is mounted to the partition that separates the upper compartment 22 from the lower compartment 24. The receptacle 34 includes a seal groove containing an o-ring seal 35 for preventing coupling fluid (e.g., degassed water) from escaping the lower compartment 24 into the upper compartment 22. The partition that separates the upper compartment 22 from the lower compartment 24 can include an optional opening 25 that can be used as a pass through between the compartments for various purposes (e.g., for sensors, wiring, electronics, water line(s), filters, etc.). The optional opening 25 can be sealed to prevent coupling fluid from escaping the lower compartment 24 into the upper compartment 22. The control arm upper end 36 interfaces with the pivot ball 42. The pivot ball 42 includes a central bore 43 that interfaces with a cylindrical outer surface of the control arm upper end 36. The control arm interface component 44 includes mating surfaces designed to interface with the pivot ball 42 so as to constrain the pivot ball 42 from translating relative to the interface component 44 while allowing the pivot ball 42 to rotate relative to the interface component 44. The interface between the pivot ball 42 and the control arm upper end 36 allows for the relative translation between these components that arises due to the rotation of the interface component 44 about or along the centerline of the actuation assembly 28 (shown in FIG. 3) and the resulting motion of the control arm 32 as it pivots within the receptacle 34.

Figure 5:
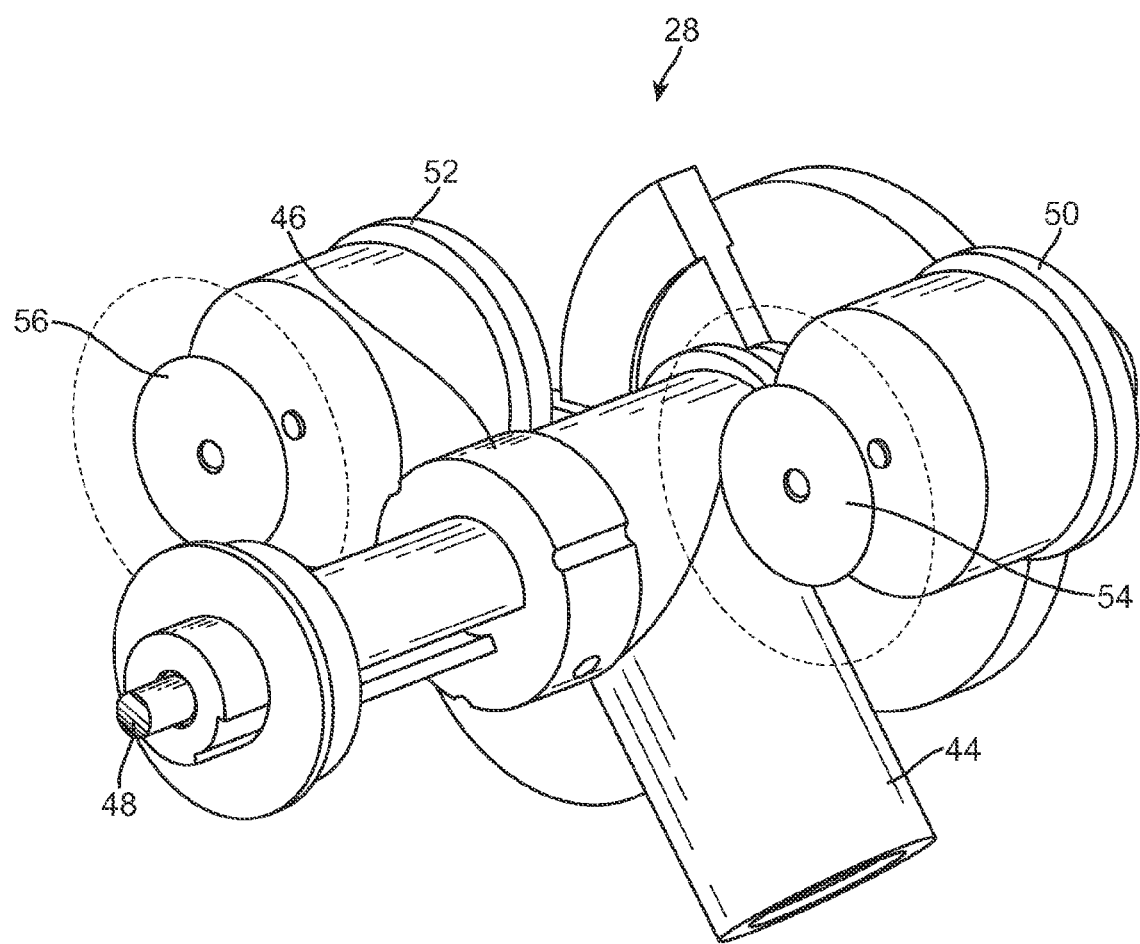
FIG. 5 is a perspective view of the actuation assembly of the ultrasound therapy head of FIGS. 2 and 3.

FIG. 5 illustrates the actuation assembly 28. The actuation assembly provides for controlled translation and rotation of the interface component 44 along and about the centerline of the actuation assembly 28. The interface component 44 is coupled with the translating/rotating hub 46 in any number of ways. As examples, the interface component 44 can include a central bore and be press-fit onto the hub 46, the interface component 44 and the hub 46 can be include interfacing splines, or the interface component 44 and the hub 46 can be combined into a single integral component. The hub 46 and the central shaft 48 are configured such that rotation of the central shaft 48 causes translation of the hub 46 along the centerline of the actuation assembly 28. The actuation assembly 28 includes two rotary motors, which include a translation motor 50 and a rotation motor 52. The translation motor 50 is rotationally coupled with the central shaft 48, thereby controlling the translation of the interface component 44 along the centerline of the actuation assembly 28. The rotation motor 52 controls the rotation of the interface component 44 about the centerline of the actuation assembly 28. A translation motor encoder 54 is used to track the rotary position of the translation motor 50 and a rotation motor encoder 56 is used to track the rotary position of the rotation motor 52.

FIGS. 6A and 6B illustrate details of the coupling between the translation motor 50 and the central shaft 48. Rotation of the translation motor 50 is transferred to the central shaft 48 by way of a translation motor output gear 58, which interfaces with a central shaft drive gear 60 that is coupled with the central shaft 48. The translation motor encoder 54 monitors the rotary position of the translation motor 50 and the central shaft 48. The central shaft drive gear 60 can be coupled with the central shaft 48 in a variety of ways (e.g., by a key or by splines).

Figure 7B:
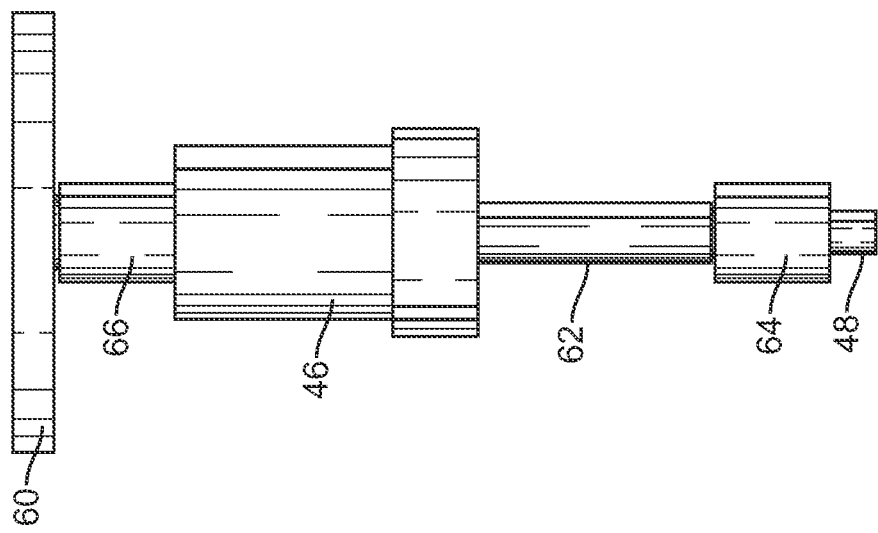
FIG. 7B is a top view of the translating/rotating hub coupled with the central shaft shown in FIG. 7A.
Figure 7A:
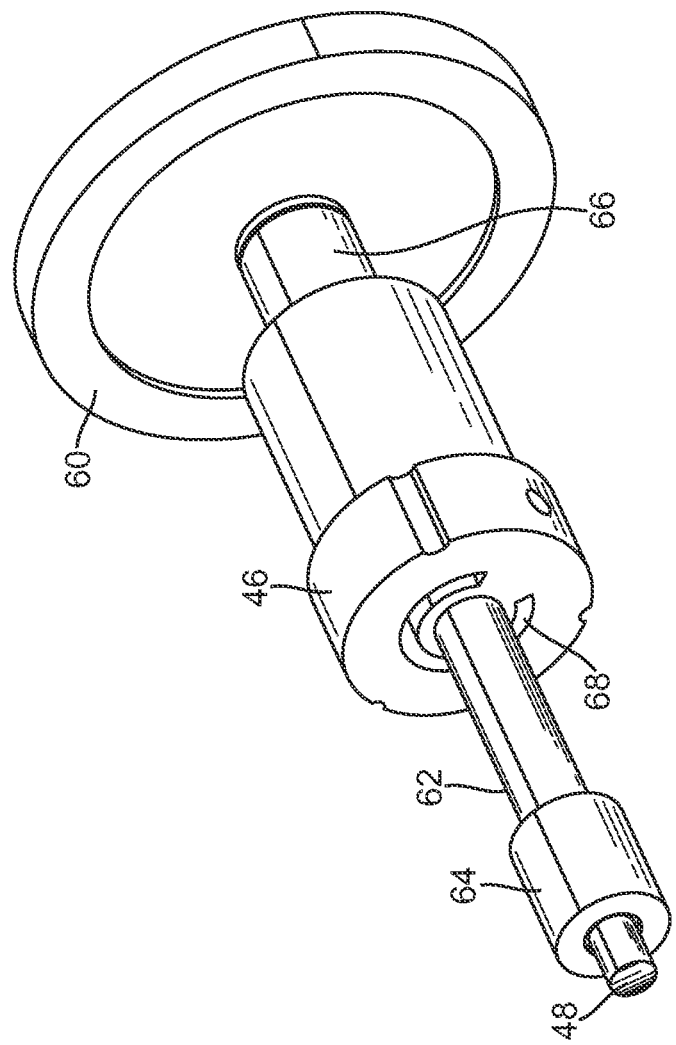
FIG. 7A is a perspective view of a translating/rotating hub of the actuation assembly of FIG. 5 in accordance with an embodiment, showing the translating/rotating hub coupled with the central shaft shown FIGS. 6A and 6B.

FIGS. 7A and 7B illustrate details of the coupling between the central shaft 48 and the translating/rotating hub 46. The central shaft 48 includes an outer surface 62 configured (e.g., by an acme screw assembly or a ball screw assembly, etc.) so as to cause translation of the translating/rotating hub 46 along the centerline of the actuation assembly 28 in response to rotation of the central shaft 48. The central shaft 48 is driven by the central shaft drive gear 60 and rotates within two end bearings 64, 66.

Figure 8:
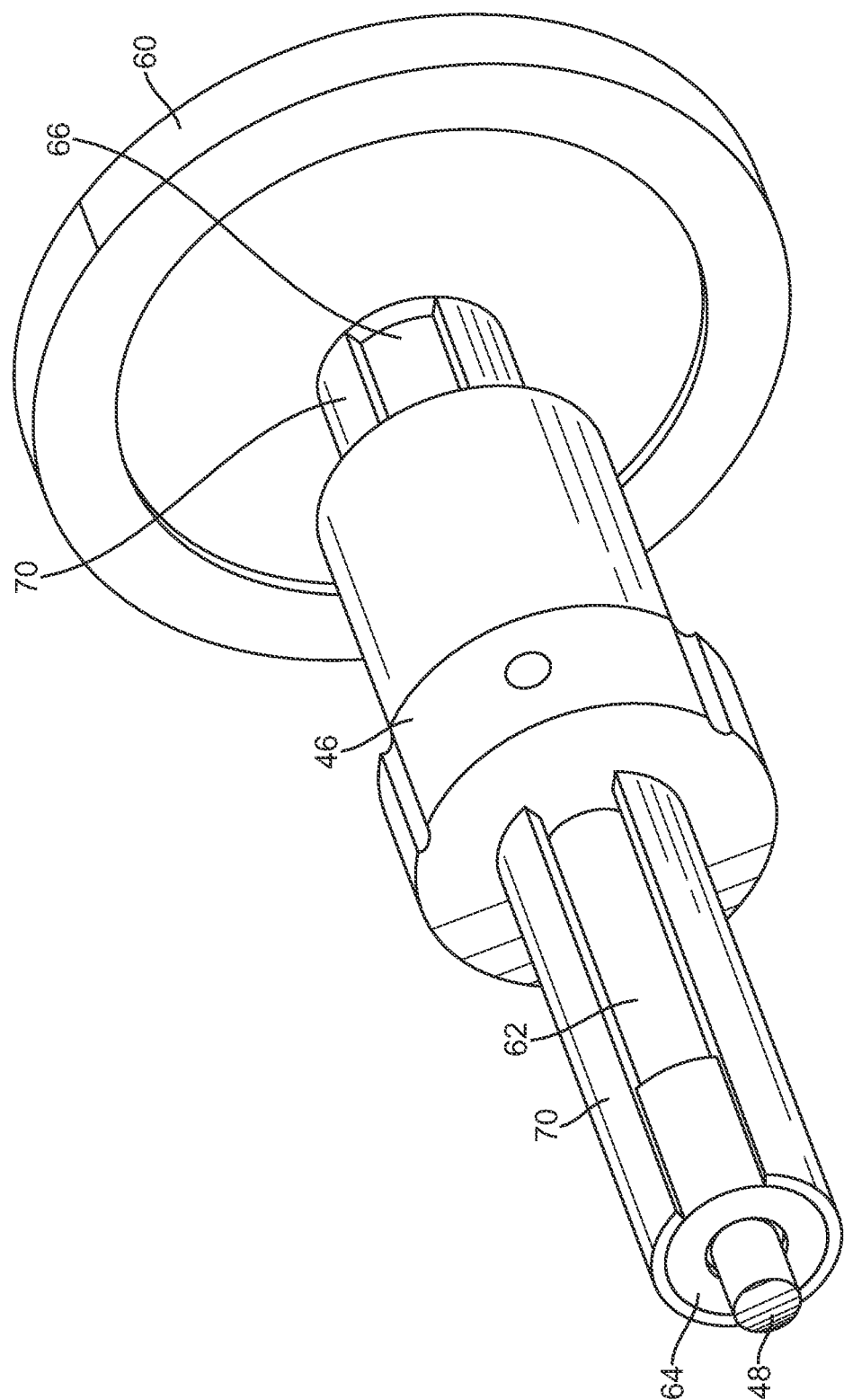
FIG. 8 is a perspective view of the translating/rotating hub as rotationally constrained by a slotted concentric shaft in accordance with an embodiment.

The hub 46 includes a partially circumferential slot 68, which is used to control the rotation of the hub 46 about the centerline of the actuation assembly 28. FIG. 8 illustrates a slotted concentric shaft 70, which interfaces with the circumferential slot 68 (shown in FIG. 7) so as to control the rotation of the hub 46 about the centerline of the actuation assembly 28. The slotted concentric shaft 70 fits within the circumferential slot 68, thereby allowing the hub 46 to translate along the slotted concentric shaft 70 while constraining the hub 46 from rotating about the slotted concentric shaft 70. The two end bearings 64, 66 provide for relative rotation between the central shaft 48 and the slotted concentric shaft 70. The slotted concentric shaft 70 includes two end counter-bores configured to accept the two-end bearings 64, 66.

In operation, rotating the central shaft 48 causes the exterior surface 62 to interact with the hub 46 thereby causing the hub 46 to translate along the centerline of the actuation assembly 28. The slotted concentric shaft 70 can be held stationary so that the hub 46 is constrained from rotating about the centerline of the actuation assembly 28 while the hub 46 translates along the centerline of the actuation assembly 28.

Figure 9:
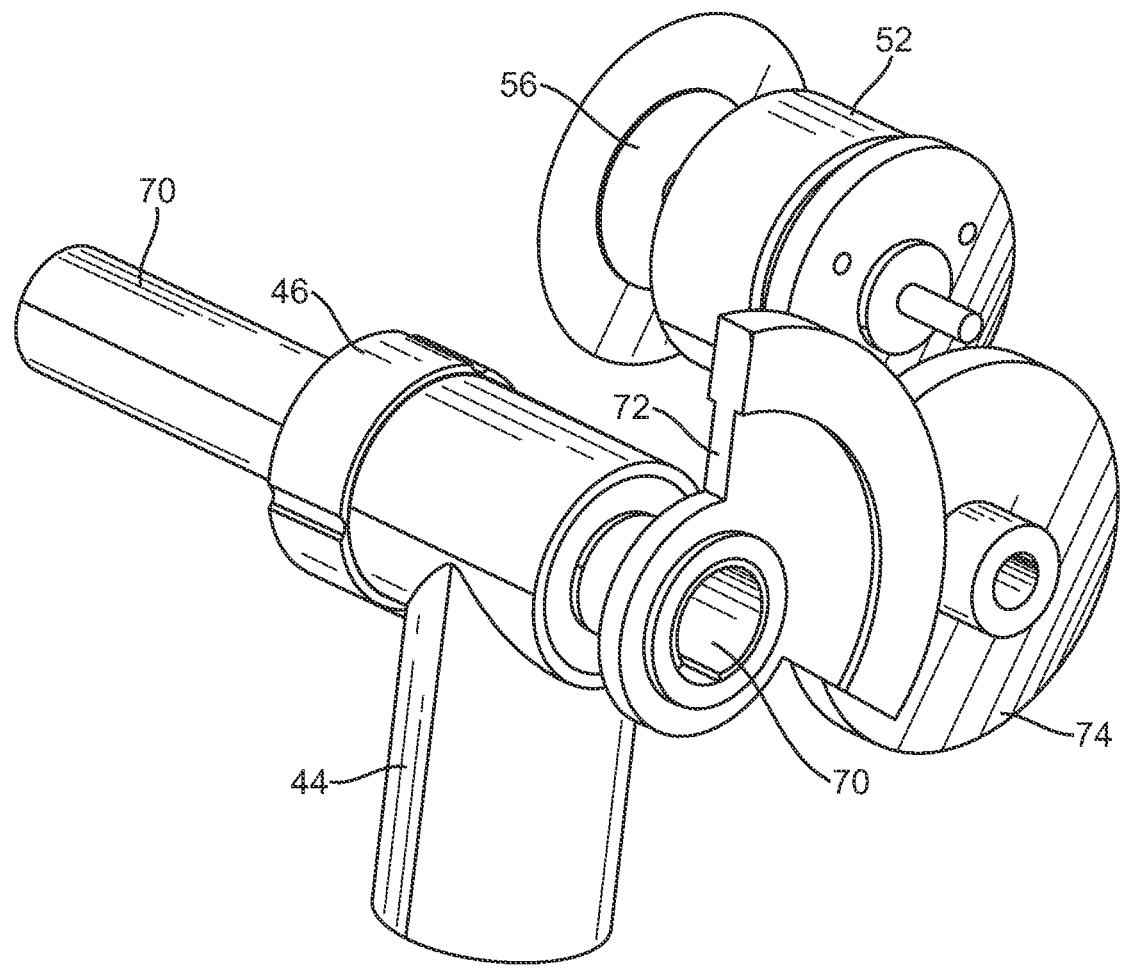
FIG. 9 is a perspective view of a control arm interface component coupled with the translating/rotating hub and associated drive mechanism for rotating the slotted concentric shaft in accordance with an embodiment.

FIG. 9 illustrates components of the actuation assembly 28 that are used to control the rotation of the slotted concentric shaft 70, and thereby control the rotation of the interface component 44. The slotted concentric shaft 70 is coupled with a partial gear 72, which includes a gear sector sufficient to rotate the slotted concentric shaft 70 through its range of motion. The partial gear 72 is driven by an idler gear 74. The idler gear 74 is driven by a pinion gear (not shown), which is driven by the rotation motor 52. The rotation motor 52 is coupled with the rotary encoder 56, which monitors the rotational position of the rotation motor 52, thereby monitoring the rotational position of the slotted concentric shaft 70, the hub 46, and the interface component 44.

Figure 10:
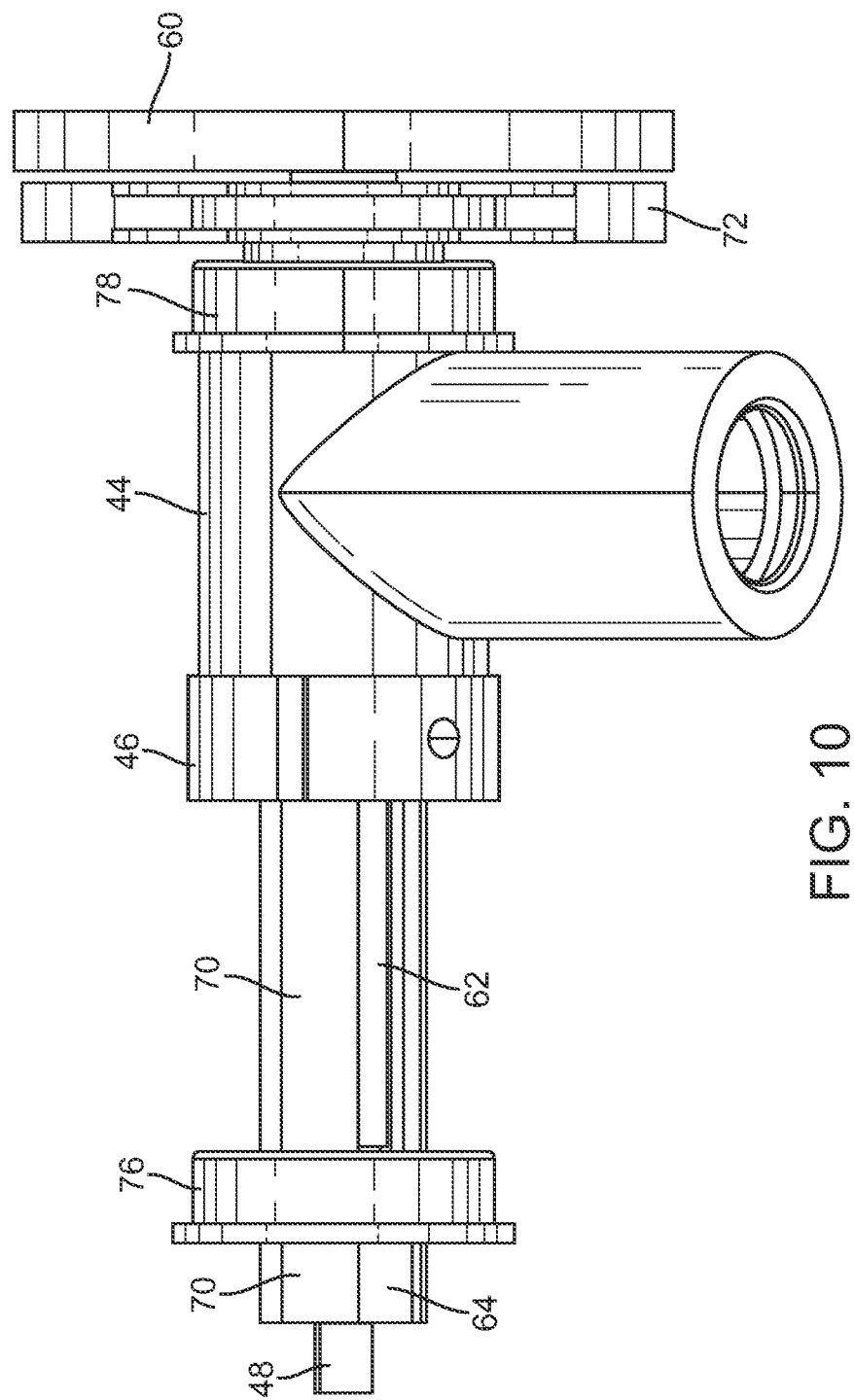
FIG. 10 is a side view illustration of a subassembly of the actuation assembly of FIG. 5, showing the control arm interface component as coupled with the central shaft and as rotationally constrained by the slotted concentric shaft.

The combined operation of the core actuation subassembly that provides for the translation and rotation of the interface component 44 is now described with reference to FIG. 10. The slotted concentric shaft 70 rotates within two support bearings 76, 78. The rotation of the slotted concentric shaft 70 is controlled by the partial gear 72, which is controlled via the rotation motor 52 as described above. The rotational position of the interface component 44 is directly controlled by the rotational position of the slotted concentric shaft 70 via the circumferential slot 68 in the translating/rotating hub 46. The rotation of the central shaft drive gear 60 relative to the partial gear 72 causes the central shaft 48 to rotate relative to the hub 46, which causes the central shaft outer surface 62 to interact with the hub 46 such that the hub 46 and the interface component 44 translate along the centerline of the actuation assembly 28.

While the actuation assembly describe above includes two motors, it could be configured to include a single motor. For example, a single motor can be used to drive two or more axels by way of two or more gear connectors. One or more clutches can be used to engage/disengage the motor with the axels that drive the translating/rotating hub. A single motor can also be used to drive the axels that drive the translating/rotating hub by way of other known interconnections (e.g., drive belts, chains, etc.).

The above described therapy head 20 provides a number of advantages. For example, the use of a pivotally mounted control arm avoids the use of complex mechanisms and seals (e.g., through the use of mating spherical surfaces), while providing the ability to vary the position/orientation of the ultrasound transducer assembly so as to direct energy over a two-dimensional region of a patient. The use of concentric rotational shafts provides for a compact actuation assembly, which in turn provides for a more compact therapy head. The use of rotary drive motors allows for the use of an electric actuation assembly, thereby avoiding the need for additional subsystems (e.g., hydraulic, pneumatic, etc.). The use of rotary encoders allows for relatively fine positional control due to the ratio of motor rotation to translation and/or rotation of the interface component. The use of a rotational mechanism allows for the use of rotary bearings, which can be selected to meet operational life requirements.

Figure 11:
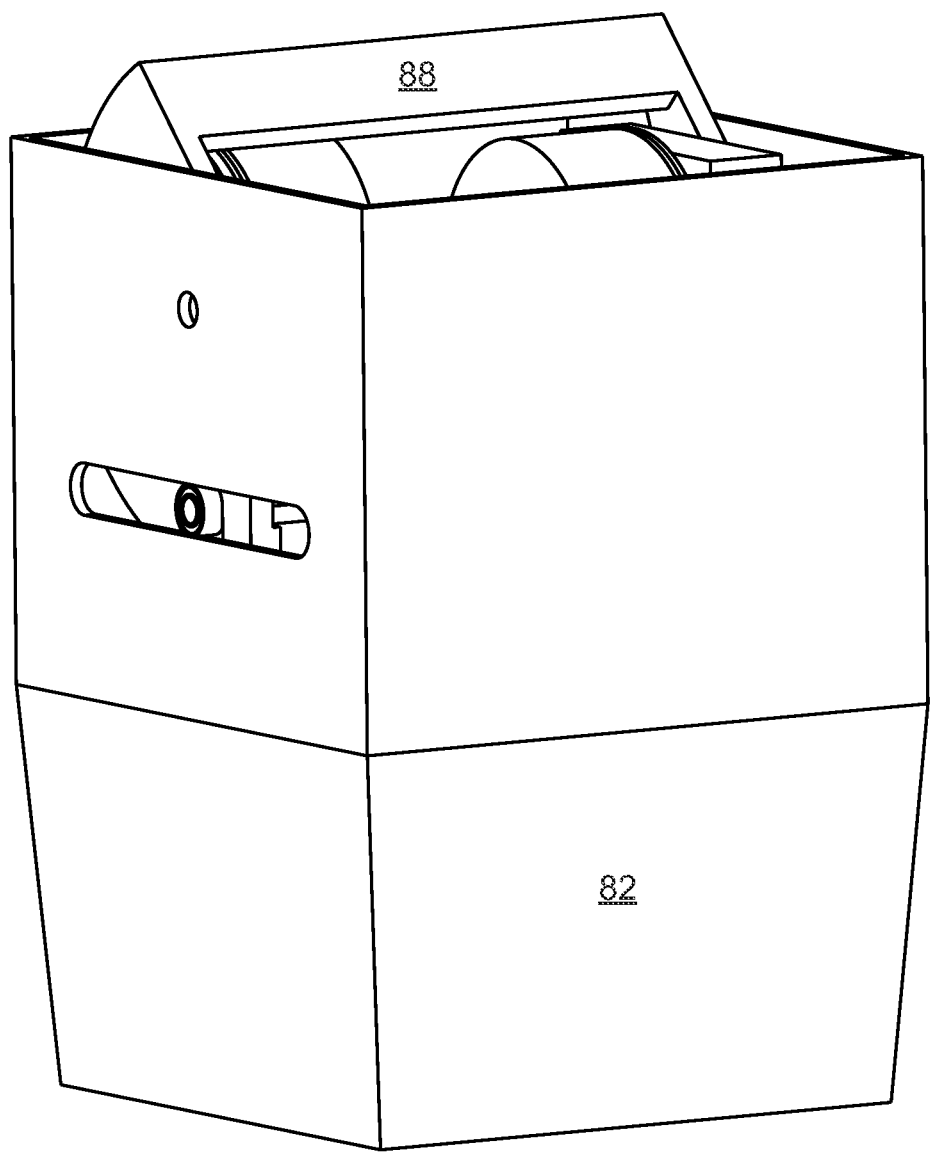
FIG. 11 is a perspective view illustration of an enclosure having an actuation assembly for repositioning/reorienting an ultrasound transducer within a therapy head in accordance with another embodiment.

An alternate embodiment of a therapy head will now be described with reference to FIGS. 11, 12, 13A, 13B, 14A, and 14B. An enclosure 82 for use in a therapy head in accordance with the alternate embodiment is shown in FIG. 11. The enclosure 82 is desirably a casing suitable for housing an actuation assembly and transducer unit within. The enclosure 82 may be a single piece part, or a multi-piece unit having access to the interior for placement of the actuation assembly and transducer components prior to final assembly. In one embodiment utilizing a motor bracket 88, the motor bracket 88 is visible at the top of the enclosure 82. The enclosure 82 has a plurality of apertures located at the top, bottom and in the side walls. The side wall apertures are desirably shaped to receive parts of the actuation assembly 80 described below.

Inside the enclosure 82 are an actuation assembly 80, a transducer 102 and a control arm 100 between the actuation assembly 80 and the transducer 102. The control arm 100 connecting the actuation assembly 80 and the transducer 102 passes through a partition 108. The actuation assembly 80 is positioned within an upper compartment 110 of the enclosure 82 while the transducer 102 is positioned within a lower compartment 112 of the enclosure 82. The control arm 100 passes through the partition 108 through a single, fixed aperture. A ball joint 104 fitted within a boot 114 is desirably positioned in the fixed aperture, and the control arm 100 passes through the ball joint 104. The actuation assembly 80 connects to the upper end of the control arm 100 via a movable lead-screw carriage 96. The actuation assembly 80 can move the lead-screw carriage 96 in two dimensions (e.g., longitudinally along a screw rail 94 and traverse relative to the screw rail 94 by moving the screw rail 94 laterally). The lead-screw carriage 96 has a variable connector on it allowing it to maintain contact with, and transmit mechanical force to, the control arm 100 when the lead-screw carriage 96 is being moved. The lead-screw carriage 96 can move the upper end of the control arm 100 like a joy stick, and cause a corresponding movement of the transducer 102 in the lower compartment 112.

Figure 12:
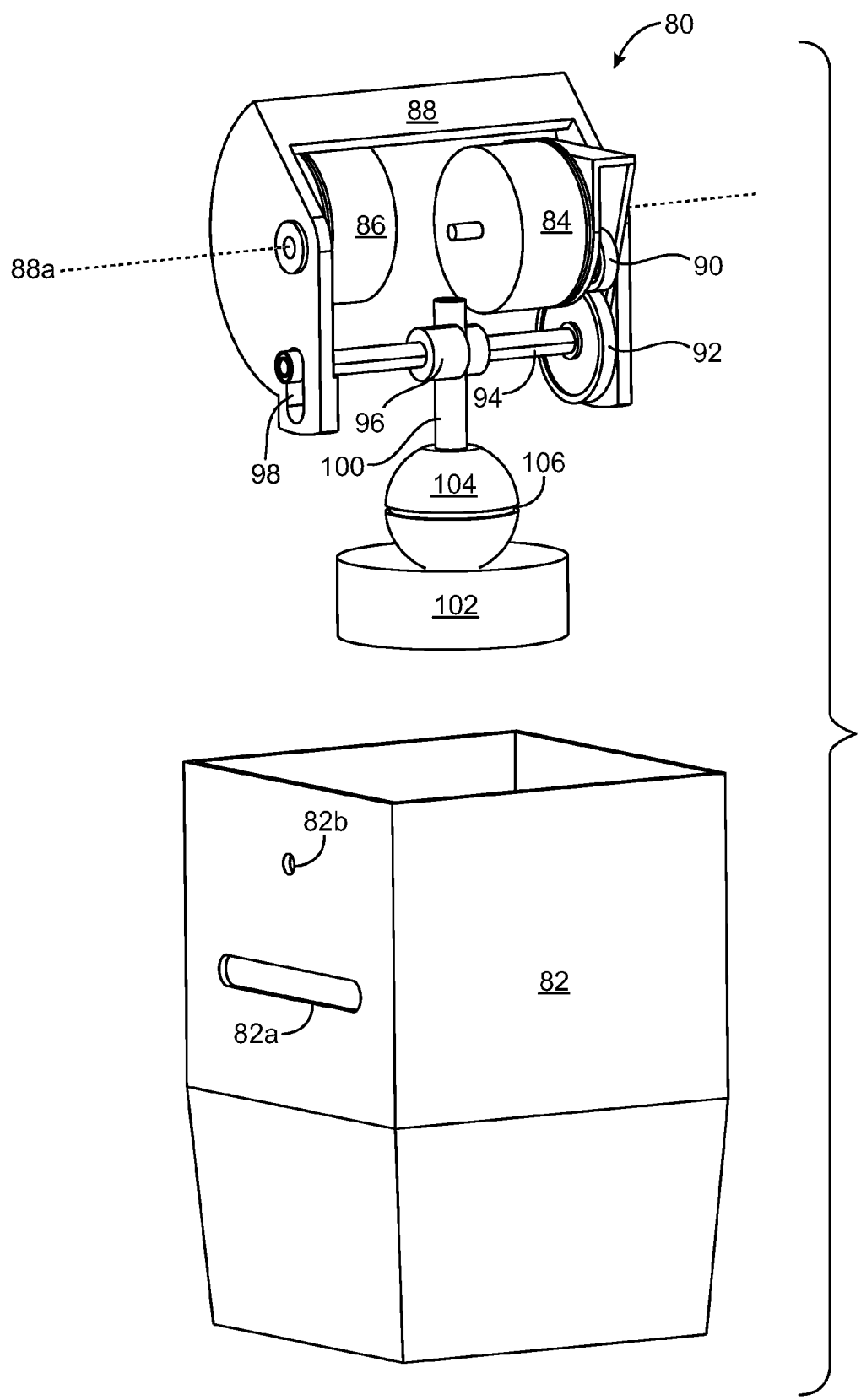
FIG. 12 is a perspective view illustration of the enclosure of FIG. 11, showing the actuation assembly displaced vertically from the enclosure.

FIG. 12 shows the actuation assembly 80 displaced vertically from the enclosure 82. The actuation assembly 80 has an axle drive motor 84, and an oscillation motor 86 mounted on the motor bracket 88. The axle drive motor 84 engages a gear mechanism 90, 92 to drive a screw rail 94. Riding on the screw rail 94 is a lead-screw carriage 96. The screw rail 94 rides within an aperture 98 in the motor bracket 88 and a slot shaped aperture 82a in the enclosure 82. The oscillation motor 86 is coupled with the motor bracket 88 and causes the motor bracket 88 to rotate around pivot axis 88a, which provides for transverse movement of the screw rail 94. Using a combination of the motors 84, 86 it is possible to move the control arm 100 like a joy stick, and move the transducer 102 about a fulcrum point within a ball joint 104. The ball joint 104 has a limit stop 106 to prevent the ball joint 104 from being moved beyond a desired position.

In some embodiments, the control arm 100 is coupled with a lead-screw carriage 96 on the actuation assembly by way of a three-axis pivot. The three-axis pivot allows the control arm 100 to axially slide up and down relative to the lead-screw carriage 96 while preventing rotation of the lead-screw carriage 96 during axial motion along the lead screw 94.

Figure 13A:
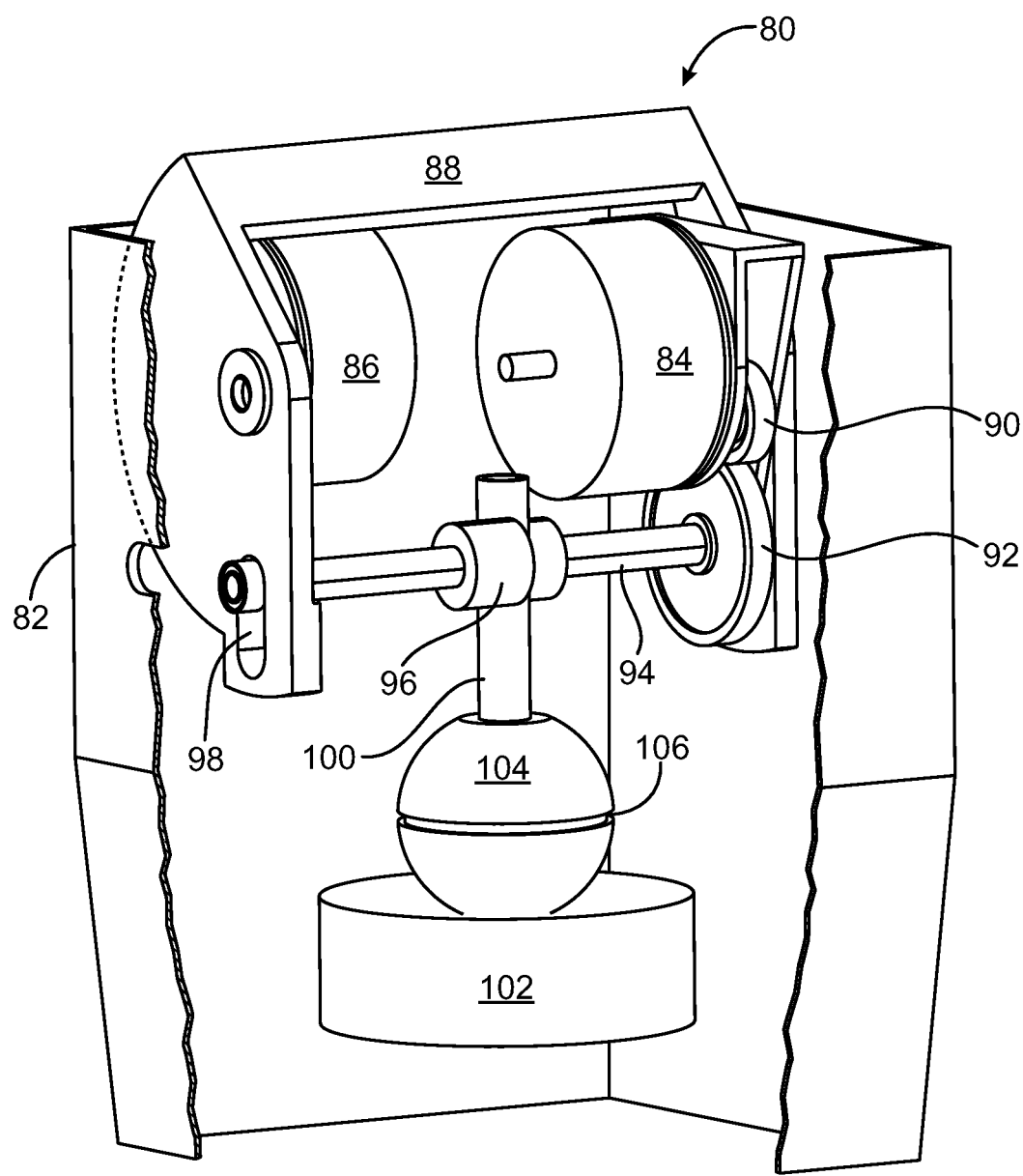
FIG. 13A is a perspective view illustration of the enclosure of FIG. 11, showing the actuation assembly disposed within a partial view of the enclosure.
Figure 13B:
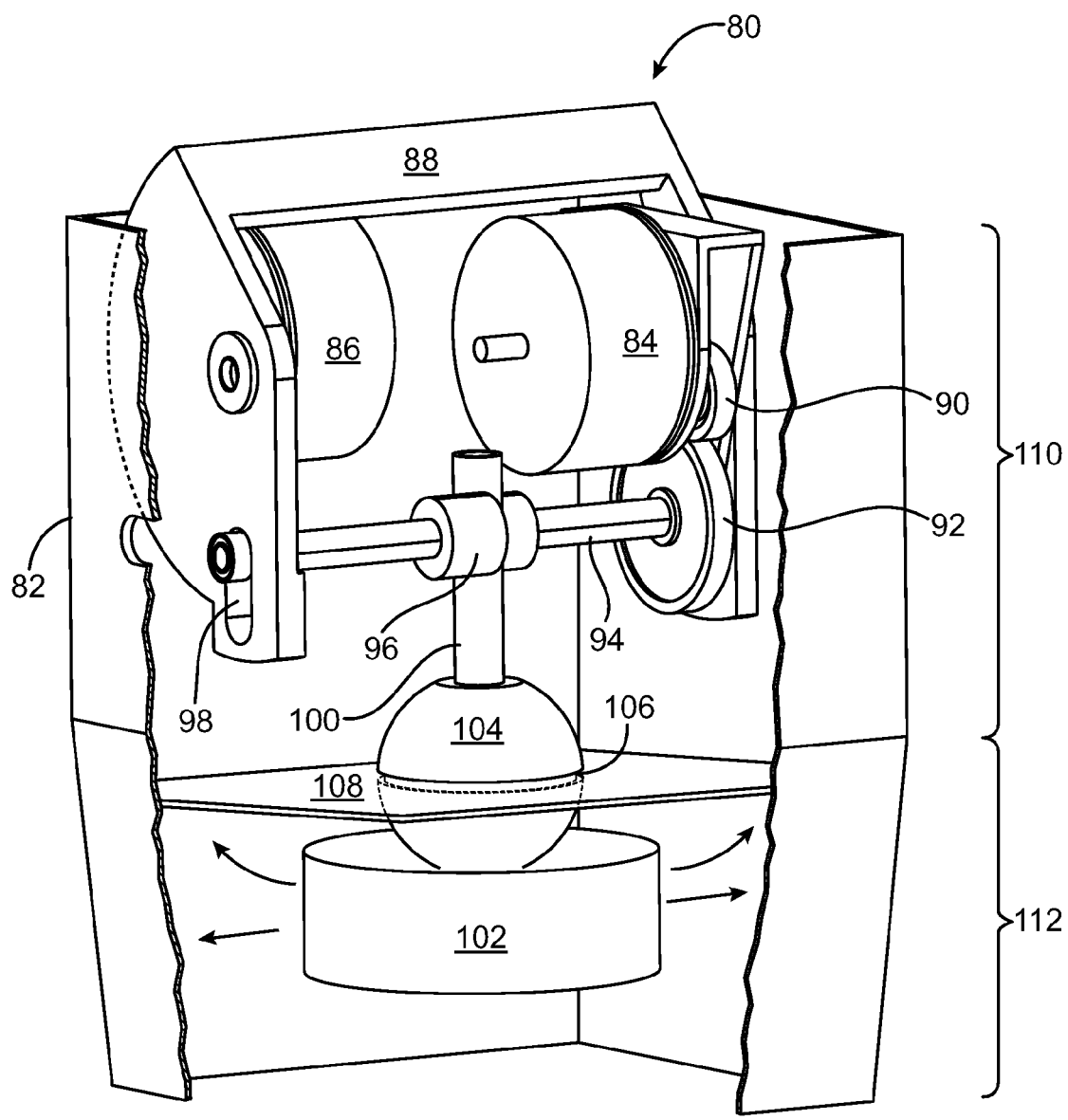
FIG. 13B is a perspective view illustration of the enclosure of FIG. 11, showing a partition between an upper compartment and a lower compartment and movement directions of an ultrasound transducer disposed within the lower compartment, in accordance with an embodiment.

FIG. 13A shows the relative position of the actuation assembly within the enclosure 82. A partition 108 separating the enclosure 82 into the upper compartment 110 and lower compartment 112 is shown in FIG. 13B. The oscillation and axial motion of an annular array style transducer 102 is shown via the arrows. The various apertures in the enclosure 82 have been omitted for clarity. The partition 108 is shown relative to the motion of the transducer 102.

The transducer 102 moves at the end of the control arm 100 and focuses ultrasound energy outside the enclosure 82. When the therapy head is properly coupled to a patient, the ultrasound energy will focus within the tissue of the patient for a desired therapeutic effect. Since the transducer 102 is on a control arm 100 of fixed length, constrained to move about a pivot point, the transducer 102 moves in a three dimensional arc creating a spherical shaped travel arc. When the transducer 102 is active, the focal zone of the transducer 102 creates a similar spherical shaped travel arc. This arc is referred to herein as the treatment arc, or the sweep area. If the transducer 102 is a fixed focus transducer, the sweep area is spherical. If the focal depth of the transducer 102 can be changed either mechanically or electronically, the sweep area shape can be changed. Either a curved sweep area or a flat sweep area can be created with the therapy heads described herein. Advantageously, a flat sweep area can be created using the actuation assembly combined with an electronically controlled array transducer.

Depth adjustment of the focal point may be achieved through a variety of techniques. The transducer's focal zone can be mechanically adjusted by changing the vertical position of the transducer. This can be accomplished by using an actuator to cause the transducer to move up and down as it goes through the arc of motion. The depth of the transducer focal zone can also be controlled electronically, by steering the focal depth of the transducer using an annular array or phased array transducer. The depth of the transducer focal zone can also be adjusted by using a lens in the cap. A curved or flat cap can be used depending on the sweep area desired. With mechanically focused transducers, HIFU lesions can be formed in tissue at a depth determined by the mechanical focus and the distance from the transducer to the skin (standoff distance). Lesions of varying depth can be obtained by varying the standoff distance with a mechanical Z-axis control mechanism. The lesion depth can also be varied by replacing the Z-axis mechanism with a transducer separated into annular rings and electrically driving each ring independently. By varying the driving energy time delay to each ring appropriately, the focus depth can be varied. Accordingly, a flat sweep area can be created using a variety of techniques even though the transducer moves about a pivot point.

There are several standard designs for the width of the individual annular rings, such as, but not limited to, equal area or equal pitch designs. The focal power of the transducer changes as the focal depth is varied. Focal power is expressed as the ratio of the focal length to the transducer aperture (f-number), so for a given aperture of an array, changing the focus electronically changes the f-number and focal power. The f-number can be kept roughly constant in more sophisticated designs by switching on or off outer rings, thus changing the aperture while also changing the focus. In the diagnostic world, this technique is known as "expanding aperture."

The design of annular array transducers presents a number of important considerations. For example, the number of rings in an annular array is important. If there are too few rings, grating lobe secondary foci will occur in the near-field and could potentially cause deleterious effects like skin burn in a therapeutic application. If there are too many rings, as in an equal area design, the outer rings become so thin so as to be practically impossible to build. The issue of secondary foci can be ameliorated greatly by building the array with a built-in mechanical focus, which also reduces the number of rings, and thus electronic channels, in the array. In simulations of annular array designs, an advantageous number of rings is shown to be 8 to 10 with an overall f-number of 1 to 2, with a 2 MHz operating frequency, and a transducer approximately 38 mm in diameter. The rings in an annular array must be acoustically isolated from each other to achieve an acceptable focal beam pattern. Acoustic isolation can be achieved by simply separating the piezoelectric layer into individual rings with an appropriate tool, such as a nested set of concentric thin steel rings mounted on the horn of an ultrasonic impact grinder. The resulting array can then be supported by a backing structure and/or an undiced matching layer(s). Solid piezoelectric materials, almost always a ceramic, when diced into sections whereby any lateral extent of the section is between ~0.7 to 5 times the thickness of the ceramic, will vibrate at different frequencies due to coupling to lateral modes. Most annular array designs end up with one or more rings with aspect ratios in the above "forbidden zone" and produce unacceptable frequency variation across the array aperture. An annular array design can make use of 1-3 composite piezoelectric ceramic materials whereby the ceramic is diced into tall, thin posts with aspect ratios on the order 0.5 and the dicing kerfs filled with polymer material such as epoxy. These materials exhibit uniform frequency response, lower levels of lateral modes, higher electromagnetic coupling constants, and higher bandwidth in good designs. In therapeutic arrays designed to withstand high operating temperatures, the polymer filler material is typically an epoxy with a high glass transition temperature. In many cases, the individual rings of the array still need to be physically separated to some degree to achieve acceptable cross-coupling levels, as discussed above. Lesions can be created in lateral extent by then moving the transducer laterally with a mechanical X-Y scanning apparatus.

The use of a cap with a lens may be combined with either the mechanical or electronic (array transducer) focal depth adjustment techniques, or used with a standard single focal distance transducer. If the cap is curved, the therapy head can be pressed against the skin so the tissue of the patient conforms to the contours of the cap. When the transducer sweeps out an area, the area treated will be equidistant from the skin surface through out the sweep area. The cap in this case has a radius designed to match that of the transducer's sweep arc. If the cap is designed with a flat lens, a standard single focal distance transducer's focal zone will sweep out a curved treatment area under the skin.

Figure 14A:
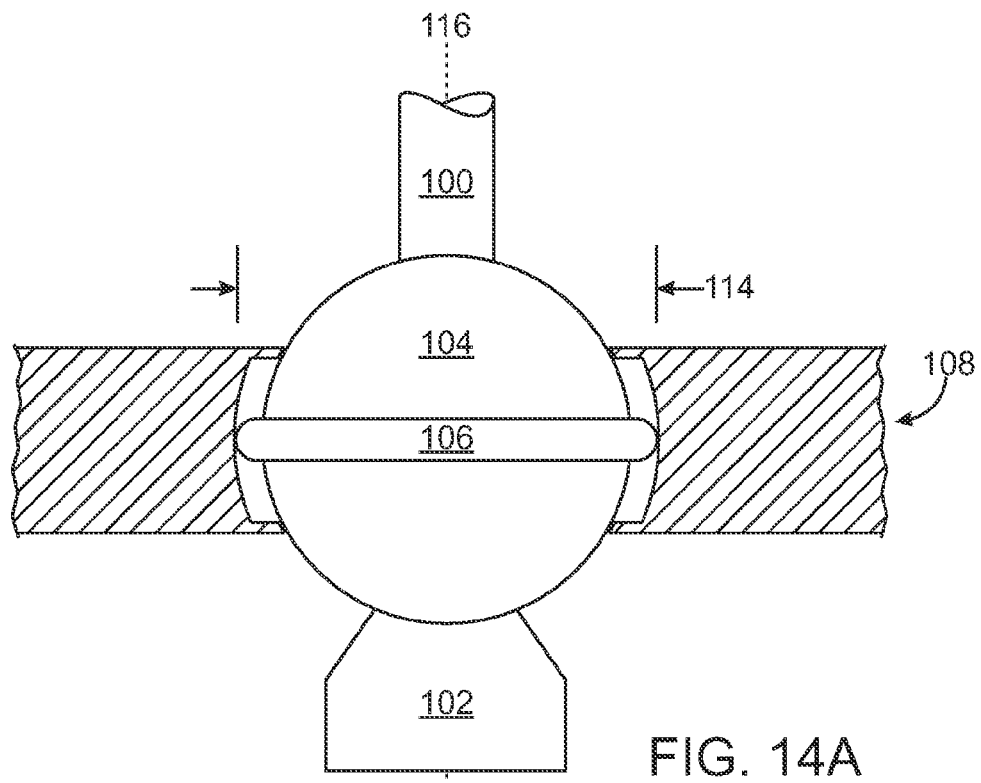
FIGS. 14A and 14B are cross-sectional views illustrating details of a coupling between a control arm and a therapy head partition and ranges of motion of the control arm in accordance with an embodiment.
Figure 14B:
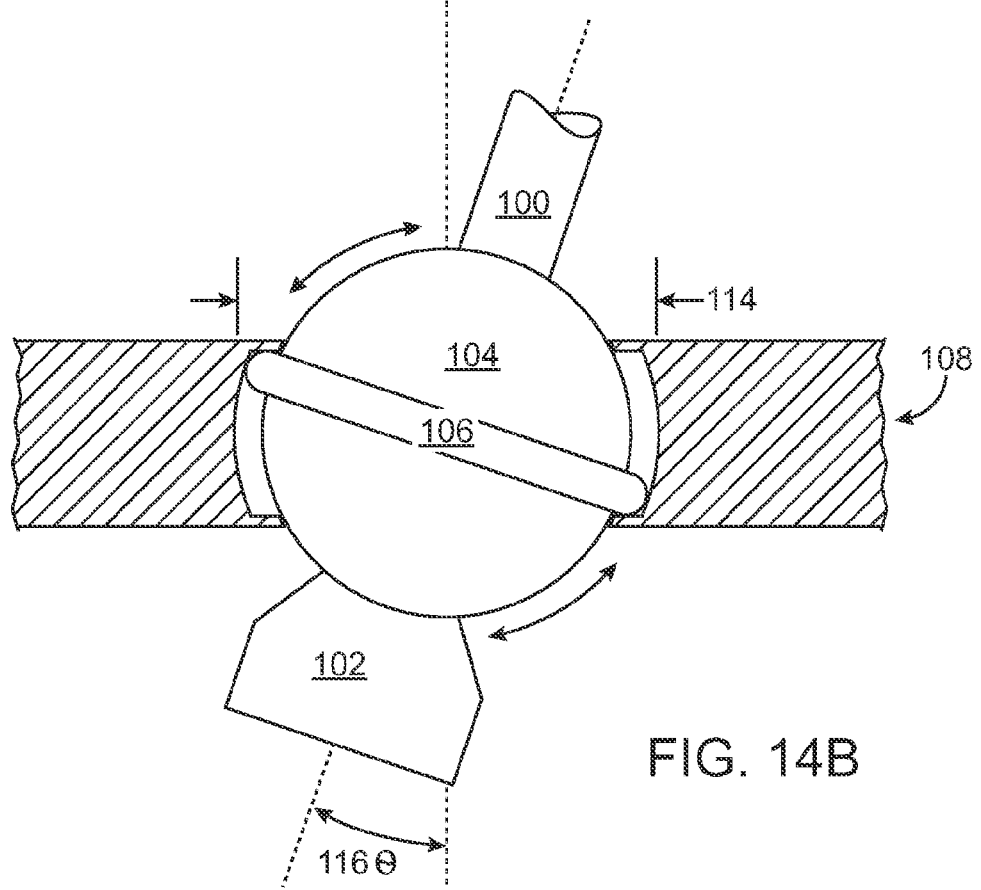

FIG. 14A illustrates the ball-joint 104 in a "neutral" position with the control arm 100 positioned vertically. The ball joint 104 is constrained by the partition 108 and surrounded by a boot 114. A hard stop or limit mechanism 106 is provided to prevent the ball joint 104 from moving outside the confines of the boot 114. Electrical control for the transducer 102 can be routed through or along the shaft 100, through the ball joint 104 and can be connected to the transducer 102. FIG. 14B illustrates the ball joint 104 at the limit of one motion with the shaft tilted to one side, and the limit mechanism 106 at the hard stop of the boot 114.

Figure 15:
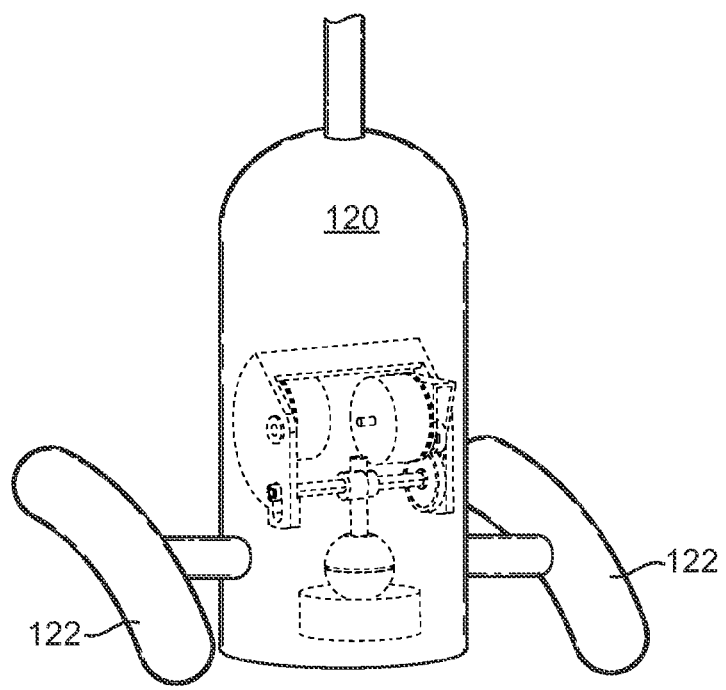
FIGS. 15, 16, and 17 illustrate therapy head handles, a rubberized jacket, and a therapy head shaped to provide an increased range of transducer motion, respectively, in accordance with embodiments.
Figure 16:
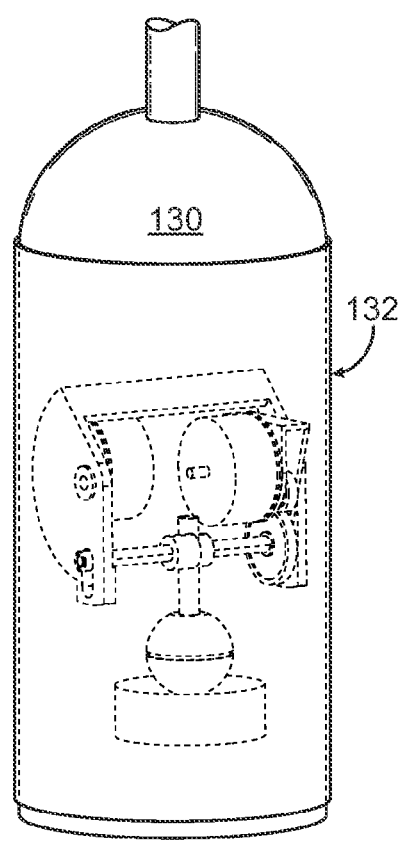
Figure 17:
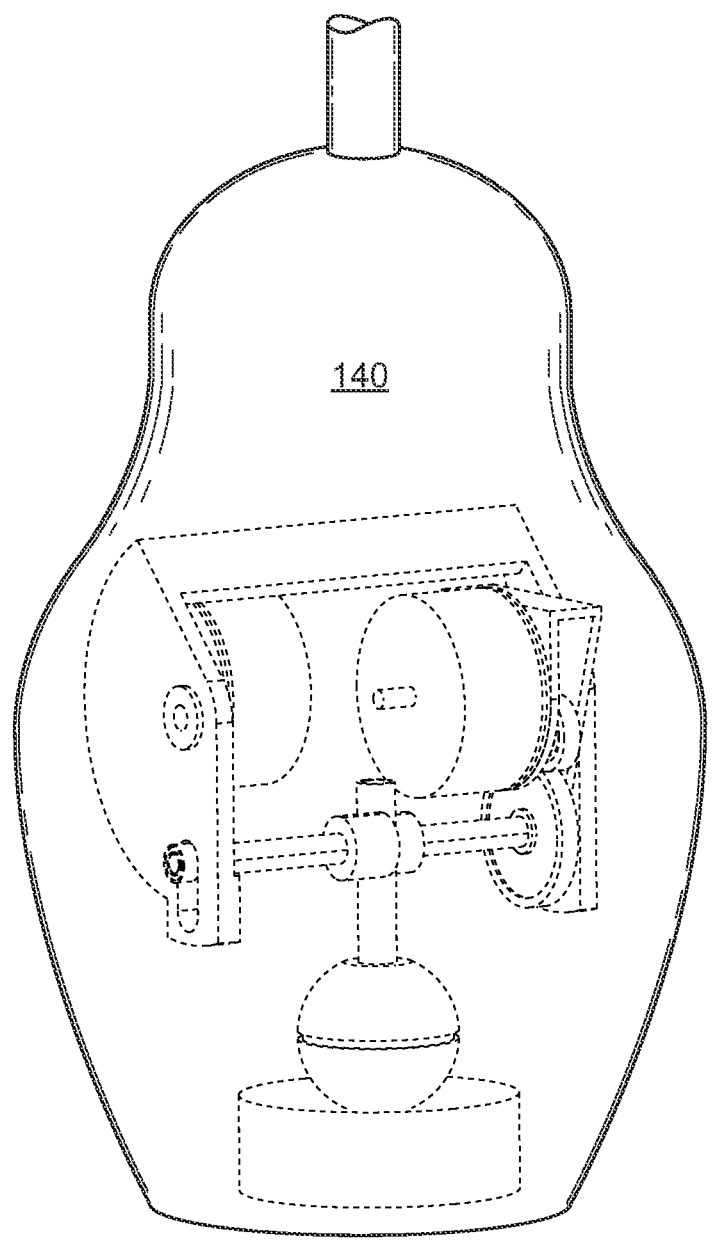

A therapy head can be configured to facilitate manipulation. For example, as illustrated in FIG. 15, a therapy head 120 can include handles 122. As illustrated in FIG. 16, a therapy head 130 can include a rubberized jacket 132 or other ergonomic fittings to assist a user in holding the therapy head with one or two hands. As illustrated in FIG. 17, a therapy head 140 can be shaped to provide for an increased range of transducer motion.

The above embodiments provide a number of advantages, For example, the use a joystick like control arm to articulate a HIFU transducer provides a design parameter that can be varied to balance the size of the actuation assembly against the accuracy required. The transducer is mounted to the control arm, which then goes through a three axis pivot that acts as a point of rotation. By varying the ratio of the distance between the pivot point and the actuation assembly and the distance between the pivot point and the transducer, it is possible to increase or decrease the amount of transducer movement that can be achieved, which can also affect the accuracy of the HIFU focal point. For example, if the distance between the pivot point and the transducer is twice the distance as that between the pivot point and the actuation assembly, the actuation assembly foot print can be reduced since it would only need to be capable of a travel distance that is half of that required for the motion profile of the transducer. The ratio of distances described above could be adjusted to provide the most efficient balance between actuation assembly size and accuracy. If the ratio is 1 to 1, then any actuation assembly free play, due to gear backlash, assembled clearances, motor free play, etc., is translated to the HIFU transducer focal point on a 1:1 ratio.

The use of the joystick like control arm also allows for the calculation of the Z-elevation change in the focal point of the transducer for any position of the control arm. An effect of the pendulum design is that as the transducer swings about the pivot point, the transducer focal point Z depth will change relative to a flat plane. This is driven by the distance between the pivot point and the transducer focal point. This distance creates an effective radius, so that the Z elevation change can be calculated as a function of actuation assembly position/rotation.

The use of the joystick like control arm also provides for straightforward integration of the actuation assembly. The control arm is mounted to the transducer and then goes through a pivot point at a known distance and ratio to the distance between the pivot point and the actuation assembly. Somewhere between the transducer and the actuation assembly, the control arm also transitions between the dry actuation assembly compartment and the wet transducer compartment. The single pivot point causes the associated surfaces to experience sliding contact, which provides the ability to use simple sealing members (e.g., o-ring seals, blade seals, etc.).

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A therapy head for application of directional energy to a patient, the therapy head comprising:
    an enclosure adapted to be manipulated by hand, the enclosure having an upper compartment and a lower compartment with a window;
    a partition separating the lower compartment of the enclosure from the upper compartment of the enclosure;
    a receptacle mounted to the partition;
    a first control arm pivotally mounted within the receptacle, the first control arm having an upper end disposed within the upper compartment, a lower end disposed within the lower compartment, and an instantaneous center of rotation between the upper end and the lower end, the first control arm being movable within the receptacle while the receptacle is sealed between the upper and lower compartments, and the first control arm being coupled with the receptacle such that the instantaneous center of rotation of the first control arm is restrained from translating relative to the receptacle;
    a second control arm in the upper compartment, the second control arm pivotally coupled with the upper end of the first control arm;
    an actuation assembly positioned within the upper compartment, the actuation assembly including a first motor and a second motor that are coupled with the second control arm for producing movement of the second control arm in a first direction and movement of the upper end of the first control arm in a second direction counter to the first direction; and
    a directional energy applicator configured to transmit the directional energy through the window, the directional energy applicator being coupled with the lower end of the first control arm,
    wherein the first control arm is configured to pivot, in response to the movement of the second control arm by the actuation assembly, within the receptacle about the instantaneous center of rotation around at least two axes for varying a position or an orientation of the directional energy applicator so as to direct the directional energy over a two-dimensional region of the patient.

2. The therapy head of claim 1, wherein the energy applicator comprises an ultrasound transducer.

3. The therapy head of claim 2, wherein the ultrasound transducer comprises an annular array or a phased array.

4. The therapy head of claim 2, wherein the ultrasound transducer comprises a high intensity focused ultrasound transducer.

5. The therapy head of claim 2, wherein the transducer has a fixed focal length, and the window is shaped based upon a treatment sweep area for the transducer.

6. The therapy head of claim 1, wherein the window comprises a lens.

7. The therapy head of claim 1, further comprising:
a fluid seal between the control arm and the receptacle.

8. The therapy head of claim 1, wherein the actuation assembly includes a centerline having a fixed position and a fixed orientation relative to the upper compartment, the first motor is configured to position the second control arm along the centerline, and the second motor is configured to rotate the second control arm about the centerline.

9. The therapy head of claim 8, further comprising:
a first rotating shaft configured to driven by the first motor, the first rotating shaft configured to control the position of second control arm along the centerline; and
a second rotating shaft configured to driven by the second motor, the second rotating shaft configured to control the rotation of the second control arm about the centerline.

10. The therapy head of claim 1, wherein the actuation assembly includes a first centerline having a fixed position and a fixed orientation relative to the upper compartment, a bracket pivotally mounted about the first centerline, and a second centerline having a fixed position and a fixed orientation relative to the bracket, the first motor is configured to rotate the bracket about the first centerline, and the second motor is configured to position the second control arm along the second centerline.

11. The therapy head of claim 10, further comprising: a rotating shaft configured to be driven by the second motor, the rotating shaft configured to control the position of the second control arm along the second centerline.

12. A medical ultrasound system comprising:
a base unit; and
a therapy head coupled with the base unit, the therapy head including:
an enclosure adapted to be manipulated by hand, the enclosure having an upper compartment and a lower compartment with a window;
a partition separating the lower compartment of the enclosure from the upper compartment of the enclosure;
a receptacle mounted to the partition;
a first control arm pivotally mounted within the receptacle, the first control arm having an upper end disposed within the upper compartment, a lower end disposed within the lower compartment, and an instantaneous center of rotation between the upper end and the lower end, the first control arm being movable within the receptacle while the receptacle is sealed between the upper and lower compartments, and the first control arm being coupled with the receptacle such that the instantaneous center of rotation of the first control arm is restrained from translating relative to the receptacle;
a second control arm in the upper compartment, the second control arm pivotally coupled with the upper end of the first control arm;
an actuation assembly positioned within the upper compartment, the actuation assembly including a first motor and a second motor that are coupled with the second control arm for producing movement of the second control arm in a first direction and movement of the upper end of the first control arm in a second direction counter to the first direction; and
a directional energy applicator configured to transmit the directional energy through the window, the directional energy applicator being coupled with the lower end of the first control arm,
wherein the first control arm is configured to pivot, in response to the movement of the second control arm by the actuation assembly, within the receptacle about the instantaneous center of rotation around at least two axes for varying a position or an orientation of the directional energy applicator so as to direct the directional energy over a two-dimensional region of the patient.

13. The system of claim 12, wherein the directional energy applicator is an ultrasound transducer, and the ultrasound transducer comprises an annular array or a phased array.

14. The system of claim 12, wherein the directional energy applicator has a fixed focal length, and the window is shaped based upon a treatment sweep area for the directional energy applicator.

15. The system of claim 12, wherein the window comprises a lens.

16. The system of claim 12, wherein the directional energy applicator comprises a high intensity focused ultrasound transducer.

17. The system of claim 12, wherein the actuation assembly includes a centerline having a fixed position and a fixed orientation relative to the upper compartment, the first motor is configured to position the control arm interface component along the centerline, and the second motor is configured to rotate the second control arm about the centerline.

18. The system of claim 17, further comprising:
a first rotating shaft configured to driven by the first motor, the first rotating shaft configured to control the position of the second control arm along the centerline; and
a second rotating shaft configured to driven by the second motor, the second rotating shaft configured to control the rotation of the second control arm about the centerline.

19. The system of claim 12, wherein the actuation assembly includes a first centerline having a fixed position and a fixed orientation relative to the upper compartment, a bracket pivotally mounted about the first centerline, and a second centerline having a fixed position and a fixed orientation relative to the bracket, the first motor is configured to rotate the bracket about the first centerline, and the second motor is configured to position the second control arm along the second centerline.

20. The system of claim 19, further comprising: a rotating shaft configured to be driven by the second motor, the rotating shaft configured to control the position of the second control arm along the second centerline.

* * * * *

UNITED STATES PATENT AND TRADEMARK OFFICE
CERTIFICATE OF CORRECTION

PATENT NO. : 8,926,533 B2
APPLICATION NO. : 12/364327
DATED : January 6, 2015
INVENTOR(S) : Craig Robert Bockenstedt et al.

Page 1 of 1

It is certified that error appears in the above-identified patent and that said Letters Patent is hereby corrected as shown below:

In the Specification:

At column 4, line number 55, change the first instance of "a" to --an--

At column 6, line number 11, after "can" delete "be"

At column 7, line number 30, change "describe" to --described--

At column 8, line number 52, change "is" to --are--

At column 11, line number 49, change "are" to --is--

In the Claims:

At column 13, claim number 9, line number 10, after "to" insert --be--

At column 13, claim number 9, line number 12, after "of" insert --the--

At column 13, claim number 9, line number 13, after "to" insert --be--

At column 14, claim number 18, line number 36, after "to" insert --be--

At column 14, claim number 18, line number 38, after "to" insert --be--

Signed and Sealed this
Ninth Day of June, 2015

Michelle K. Lee
*Director of the United States Patent and Trademark Office*